(12) United States Patent
Fukuma et al.

(10) Patent No.: US 7,159,984 B2
(45) Date of Patent: Jan. 9, 2007

(54) SUBJECTIVE OPTOMETRIC APPARATUS

(75) Inventors: Yasufumi Fukuma, Tokyo (JP);
Yukihiro Noda, Tokyo (JP); Yasuo Kato, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 701 days.

(21) Appl. No.: 10/639,441

(22) Filed: Aug. 13, 2003

(65) Prior Publication Data

US 2004/0032567 A1    Feb. 19, 2004

(30) Foreign Application Priority Data

| Aug. 14, 2002 | (JP) | ............................. 2002-236642 |
| Aug. 14, 2002 | (JP) | ............................. 2002-236643 |
| Aug. 21, 2002 | (JP) | ............................. 2002-240368 |
| Aug. 30, 2002 | (JP) | ............................. 2002-252579 |

(51) Int. Cl.
*A61B 3/04* (2006.01)
*A61B 3/02* (2006.01)

(52) U.S. Cl. ........................ 351/227; 351/222; 351/245

(58) Field of Classification Search .................. 351/58, 351/69, 141, 222–245
See application file for complete search history.

(56) References Cited

U.S. PATENT DOCUMENTS

| 1,440,799 | A | * | 1/1923 | Ryan ............................. 351/66 |
| 1,545,847 | A | * | 7/1925 | Parsons ....................... 351/229 |
| 2,103,340 | A | * | 12/1937 | Schneck ....................... 351/228 |
| 2,147,448 | A | * | 2/1939 | Lee ............................. 351/229 |
| 2,317,873 | A | * | 4/1943 | Alger .......................... 351/227 |
| 2,322,878 | A | * | 6/1943 | Peck et al. ................. 351/235 |
| 2,447,936 | A | * | 8/1948 | Ellis ............................. 351/229 |
| 2,798,408 | A | * | 7/1957 | Ellis et al. ................... 351/239 |
| 3,904,280 | A | * | 9/1975 | Tate, Jr. ....................... 351/211 |

FOREIGN PATENT DOCUMENTS

JP        2002-143092        5/2002

* cited by examiner

*Primary Examiner*—Charles A Marmor, II
*Assistant Examiner*—John R Sanders
(74) *Attorney, Agent, or Firm*—Armstrong, Kratz, Quintos, Hanson & Brooks, LLP

(57) ABSTRACT

Disclosed is a subjective optometric apparatus in which the earpiece members and the nose pad member for attaching the main body of the device to the subject can be easily adjusted without involving any effort. The subjective optometric apparatus has a horizontal frame and an inner tube inserted into the horizontal frame, with a support bar for supporting a nose pad member being passed through the horizontal frame and the inner tube. In a state in which the inner tube is being biased by a spring, a rubber member provided in a through-hole of the inner tube abuts the peripheral surface of the support bar to lock the support bar, thereby bringing the nose pad member into a locked state. Further, when a push-button is pushed in against the biasing force of the spring, the inner tube is displaced and the rubber member is detached from the peripheral surface of the support bar, with the result that the nose pad member is released from the locked state and becomes capable of being displaced.

4 Claims, 23 Drawing Sheets

SECT. A-A

SECT. A-A

SUBJECTIVE OPTOMETRIC APPARATUS

BACKGROUND OF THE INVENTION

1. Field of the Invention

The present invention relates to a subjective optometric apparatus and, more specifically, to a subjective optometric apparatus that the subject can wear like glasses.

2. Description of the Related Art

Conventionally, ophthalmic operators like oculists measure various refraction characteristics of the eye to be examined by using an objective refractometer and a subjective optometric apparatus such as a vision tester, and, on the basis of the refraction characteristics thus obtained, prescription values for glasses suitable for the eye, such as spherical degree S, cylindrical degree C., and axial angle A of cylinder axis, are determined.

The above-mentioned subjective optometric apparatus contains in its casing a turret with a number of lenses of different refractive powers arranged circumferentially. By rotating this turret by a predetermined angle, an arbitrary one of these lenses is selectively set in front of the eye to be examined. The operator asks the subject about the way he or she sees through the selected glass, and repeats such inquiry, successively selecting different lenses. In this way, the refraction characteristics of the eye are examined.

It is to be noted that it is not always desirable to adopt the refraction characteristics (or prescription values) thus obtained by the above-described subjective optometric apparatus as they are as the prescription values for the glass to be actually prescribed.

The prescription values obtained by this subjective optometric apparatus are determined on the basis of the results of judgments made as to whether the selected lens of the subjective optometric apparatus enable the subject to make a normal visual recognition of symbols, characters or the like on an eye chart at a distance, for example, of 5 m. That is, the refraction characteristics thus obtained are ones obtained through testing of vision with respect to an object at a distance, i.e., a so-called far vision test.

In the actual use of prescribed glasses, not only far vision but also vision for a nearby object is required as in the case of reading a newspaper at hand or checking any surface irregularity of the ground on which the user stands. When thus looking at a nearby object, an excessive adjusting performance is required of the eye. Thus, with the prescribed values obtained through the far vision test alone, the user can experience an extreme fatigue in the eye, dizziness, or headache.

Thus, it is necessary to rectify to some degree the balance between far vision and near vision. In view of this, an adjustment inspection is executed in which the subject wears a spectacle-shaped trial frame on his or her face, and in which lenses of refraction characteristics close to the prescription values are successively attached to the trial frame to make an inquiry as to the way the subject sees objects at a distance and nearby ones through these lenses to thereby determine final prescription values.

However, it takes time to thus perform far vision test and adjustment inspection, resulting in a prolonged inspection.

In view of this, the present inventors have developed a subjective optometric apparatus substantially reduced in size to make it possible to perform both far vision test and near vision test with a single apparatus.

This subjective optometric apparatus uses an Alvarez lens.

An Alvarez lens consists of two optical elements (e.g. phase plates) each of which has one surface formed in an aspherical configuration that can be expressed by the equation: $x = A\{(1/3)y^3 + yz^2\}$ and the other surface formed flat.

In arranging the two optical elements constituting the Alvarez lens, they are rotated by 180 degrees with respect to each other, with their aspherical surfaces being opposed to each other. By displacing (moving) the two optical elements in opposite directions by the same displacement amount (movement amount), a continuous variation in refractive power is realized (See U.S. Pat. No. 3,305,294).

By using this Alvarez lens instead of the turret, it is possible to achieve such a reduction in size and weight that the subject can wear the subjective optometric apparatus main body.

Incidentally, to enable the subject to wear the subjective optometric apparatus on the face as in the case of a trial frame, it is necessary to provide the earpiece members, nose pad member, etc. in the main body of the device.

In many cases, the positions of the ears, the shape and height of the nose, and the positional relationship between the ears and the nose differ from subject to subject. Thus, it is necessary for the earpiece members and the nose pad member to exhibit a certain fixed movable range to allow positional adjustment, etc.

It is to be noted, however, that in the case in which a function to adjust the positions of the earpiece members, etc. is simply provided, the operator moves his or her hand around the face of the subject during adjustment. Thus, when the adjustment of the members take time, it may give discomfort to the subject.

At the same time, a prolonged adjusting operation would be a waste of time and labor for the operator.

SUMMARY OF THE INVENTION

The present invention has been made in view of the above problem in the prior art. It is accordingly an object of the present invention to provide a subjective optometric apparatus in which, when the subject wears the main body of the device, it is possible to easily adjust the earpiece members and the nose pad member without involving much labor.

In order to solve the above-mentioned problem, according to a first aspect of the present invention, there is provided a subjective optometric apparatus characterized by including: a main body; an Alvarez lens provided in the main body, the Alvarez lens having its refraction characteristics continuously changed in response to relative displacement of a pair of optical elements; earpiece members to be placed on the ears of a subject and a nose pad member to be held in contact with the nose of the subject, the earpiece members and the nose pad member being provided in the main body and having fixed movable ranges so as to allow adjustment according to a positional relationship between the ears and the nose of the subject; and a lock mechanism for switching the earpiece members and the nose pad member with a single operation between an unlocked state which allows the earpiece members and the nose pad member to move freely within the movable ranges and a locked state in which the earpiece members and the nose pad member are fixed at desired positions within the movable ranges.

Here, the refraction characteristics refer to characteristics related to prescription values for glasses, such as spherical degree S, cylindrical degree C., and axial angle A of cylinder axis, or may also refer to these prescription values themselves.

The Alvarez lens consists of two optical elements (e.g. phase plates) each of which has one surface formed in an aspherical configuration that can be expressed by the equation: $x = A\{(1/3)y^3 + yz^2\}$ and the other surface formed flat.

The two optical elements constituting the Alvarez lens are maintained in a state in which they are rotated by 180 degrees with respect to each other, with their aspherical surfaces being opposed to each other. By displacing (moving) the two optical elements in opposite directions by the same displacement amount (movement amount), a continuous variation in refractive power is realized (See U.S. Pat. No. 3,305,294).

Regarding the earpiece members, the term fixed movable range refers, for example, to a predetermined rotation range in which rotation around the portion mounted to the main body is allowed. Regarding the nose pad member, the term fixed movable range refers, for example, to the range allowing movement from the main body toward the nose of the subject. Such movable ranges may be determined from data previously obtained from a plurality of subjects.

Note, however, that, regarding the subjective optometric apparatus of the present invention, what has been stated above as examples should not be construed restrictively.

By using the subjective optometric apparatus according to the first aspect of the invention constructed as described above, it is possible to perform both far vision test and near vision test, with the main body of the subjective optometric apparatus being on the face of the subject like a trial frame due to the provision of the earpiece members and the nose pad member.

Further, the lock of the lock mechanism may be canceled to make the earpiece members and the nose pad member movable within the movable range. In this movable state, the main body of the subjective optometric apparatus is attached to the face of the subject, and the lock mechanism is switched to the locked state while matching the position of the subject eye with the position of the eye examination hole of the subjective optometric apparatus, with the earpiece members and the nose pad member respectively abutting the ears and nose of the subject, whereby it is possible to fit the subjective optometric apparatus to each subject solely through one operation on the lock mechanism.

Thus, it is possible to adjust the attachment state for each subject by a simple operation and in a very short time, whereby the burden on the operator is relieved, and the subject is spared excessive stress.

Further, according to a second aspect of the present invention, in the first aspect of the invention, the subjective optometric apparatus is characterized in that: the subjective optometric apparatus is equipped with a forehead rest member to be held in contact with the forehead of the subject when the main body is attached to the subject; the forehead rest member has a fixed-movable range which allows its adjustment according to a positional relationship between the forehead rest and the forehead of the subject; and the lock mechanism switches, in synchronization with the switching of the earpiece members and the nose pad member between the unlocked state and the locked state, the forehead rest member between an unlocked state which allows the forehead rest member to move freely within the movable range and a locked state in which the forehead rest member is fixed at a desired position within the movable range.

In the subjective optometric apparatus according to the second aspect of the invention, constructed as described above, it is possible to abut, in addition to the earpiece members and nose pad member, the forehead rest member to the face (forehead) of the subject, whereby, when attached to the face of the subject like a trial frame, the subjective optometric apparatus is in more intimate contact with the face, thereby preventing the subjective optometric apparatus from slipping down.

Further, the switching between the locked and unlocked state of the forehead rest member by the lock mechanism is operationally connected with the switching between the locked and unlocked state of the earpiece members and the nose pad member, so that there is no need to individually perform the switching operation on the forehead rest member, thus avoiding an increase the burden of the operation of the operator.

Further, according to a third aspect of the present invention, there is provided a subjective optometric apparatus characterized by including: a main body; an Alvarez lens provided in the main body, the Alvarez lens having its refraction characteristics continuously changed in response to relative displacement of a pair of optical elements; earpiece members to be placed on the ears of a subject and a forehead rest member to be held in contact with the forehead of the subject, the earpiece members and the forehead rest member being provided in the main body and having fixed movable ranges so as to allow adjustment according to a positional relationship between the ears and the forehead of the subject; and a lock mechanism for switching the earpiece members and the forehead rest member with a single operation between an unlocked state which allows the earpiece members and the forehead rest member to move freely within the movable ranges and a locked state in which the earpiece members and the forehead rest member are fixed at desired positions within the movable ranges.

By using the subjective optometric apparatus according to the third aspect of the invention constructed as described above, with the earpiece members and the forehead rest member, it is possible to perform both far vision test and near vision test, with the main body of the subjective optometric apparatus being on the face of the subject like a trial frame.

Further, the lock of the lock mechanism may be canceled to make the earpiece members and the forehead rest member movable within the movable range. In this movable state, the main body of the subjective optometric apparatus is attached to the face of the subject, and the lock mechanism is switched to the locked state while matching the position of the subject eye with the position of the eye examination hole of the subjective optometric apparatus, with the earpiece members and the forehead rest member respectively abutting the ears and forehead of the subject, whereby it is possible to fit the subjective optometric apparatus to each subject solely through one operation on the lock mechanism.

Thus, it is possible to adjust the attachment state for each subject by a simple operation and in a very short time, whereby the burden on the operator is relieved, and the subject is spared excessive stress.

Further, according to a fourth aspect of the present invention, in any one of the first to third aspects of the invention, the subjective optometric apparatus is characterized in that the automatic lock mechanism includes biasing means for biasing the device to be in the locked state.

In the subjective optometric apparatus according to the fourth aspect of the invention, constructed as described above, the operator attaches the subjective optometric apparatus to the subject, with the lock mechanism being retained in the unlocked state against the biasing force of the biasing means, and the lock mechanism is automatically restored to the locked state by the biasing means by canceling this retention, so that there is no need for the operator to perform the operation of switching the lock mechanism to the unlocked state. Thus, it is possible to achieve an improvement in operability for the lock mechanism.

DESCRIPTION OF THE PREFERRED EMBODIMENTS

Embodiments of the subjective optometric apparatus of the present invention will now be described with reference to the drawings.

[First Embodiment]

Figure 1:
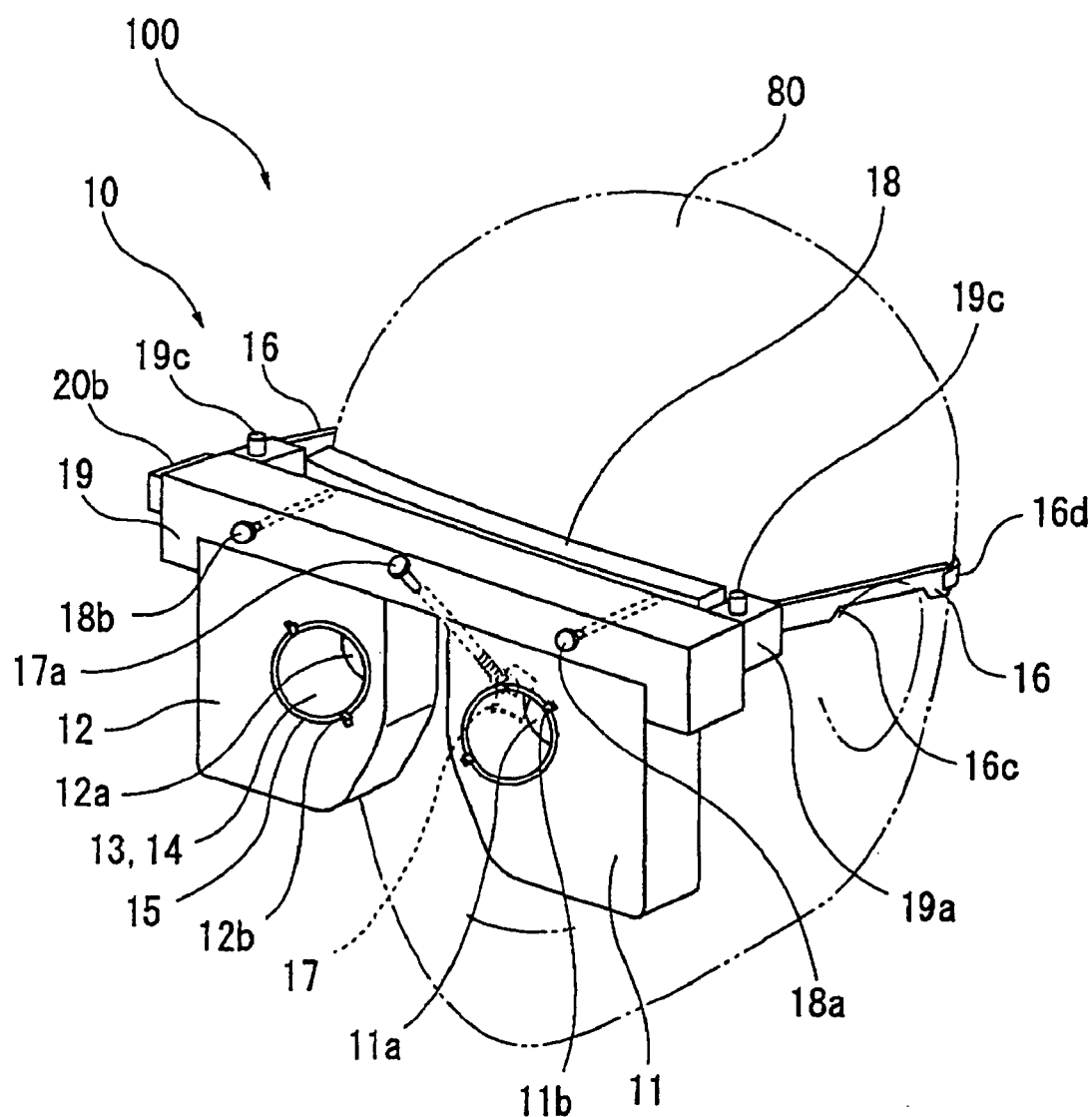
FIG. 1 is a schematic diagram showing a subjective optometric apparatus according to the present invention.

FIG. 1 is a schematic diagram showing a subjective optometric apparatus according to an embodiment of the present invention.

Figure 2:
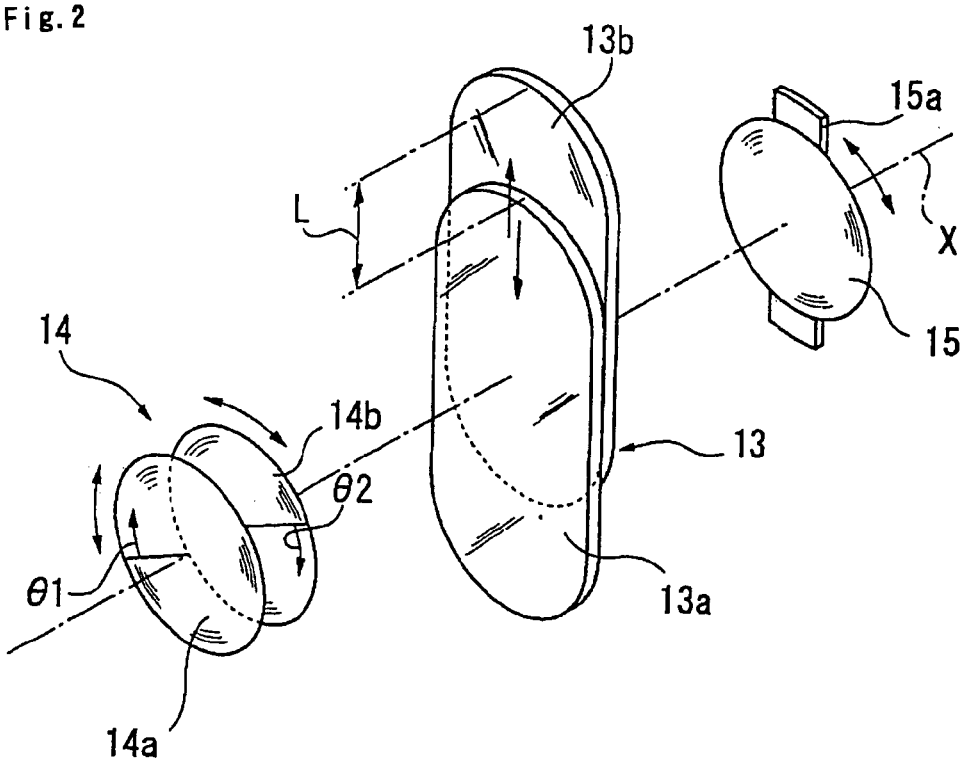
FIG. 2 is a schematic diagram showing an optical system provided inside the casing of the subjective optometric apparatus shown in FIG. 1.

In the drawing, a subjective optometric apparatus 100 is equipped with a main body 10 having casings 11 and 12 each containing an Alvarez lens 13 and a Vcc lens 14 as shown in FIG. 2. Further, on the outer side of the casings 11 and 12, (a plurality of) shift lenses 15 are provided so as to be selectively detachable. Further, the subjective optometric apparatus 100 is equipped with temples (earpiece members) 16 for suspending the main body 10 from the ears of a subject 80, a nose pad member 17 to be held in contact with the nose of the subject 80, and a forehead rest member 18 to be held in contact with the forehead of the subject 80.

Eye examination windows 11a and 12a are respectively formed in the casings 11 and 12. The subject 80 wearing the main body 10 of the subjective optometric apparatus 100 looks out of the optometric windows 11a and 12a through the Alvarez lenses 13, the Vcc lenses 14, and the shift lenses 15 to visually recognize an eye chart or the like.

To match the distance between the optometric windows 11a and 12a with the distance between the pupils (PD) of the subject 80, the casings 11 and 12 are supported so as to be longitudinally slidable along a horizontal frame 19 at the top of the main body 10.

As shown in FIG. 2, each Alvarez lens 13 is composed of a pair of transparent optical elements (for example, phase plates) 13a and 13b superimposed one upon the other. The superimposition surfaces (opposing surfaces) of these optical elements 13a and 13b are formed as cubically curved surfaces that can be expressed by the equation: $x = A\{(1/3)y^3 + yz^2\}$. The two optical elements 13a and 13b are vertically displaced relative to each other in a plane perpendicular to the optical axis X thereof, whereby it is possible to continuously vary the refraction obtained through optical synthesis of the optical elements 13a and 13b.

In this embodiment, the maximum relative displacement amount in the vertical direction of the two optical elements 13a and 13b, Lmax is, for example, approximately 12 mm.

Due to this displacement amount of 12 mm, it is possible to continuously vary the spherical degree S1 of the Alvarez lens 13 within a range of −10 D (diopter) to +10 D.

Further, the Vcc lens 14, arranged coaxially with the optical axis X of the Alvarez lens 13, is composed of two cylinder lenses 14a and 14b provided so as to be rotatable around the optical axis X (by rotational displacements of θ1 and θ2, respectively). In the Vcc lens 14, it is possible to vary the cylindrical degree C. and the axial angle A of the cylindrical axis by varying the rotational displacements of the cylinder lenses 14a and 14b.

The relative displacement L of the optical elements 13a and 13b of the Alvarez lens 13 and the rotational displacements of θ1 and θ2 of the Vcc lens 14 may be effected manually or electrically by incorporating motors in the casings 11 and 12.

Formed in the optometric windows 11a and 12a are shift lens attachment portions 11b and 12b for attaching, selectively and detachably, the shift lenses 15 for uniformly shifting spherical degree S.

Tab portions 15a of the shift lenses 15 are fitted into the shift lens attachment portions 11b and 12b, whereby the shift lenses 15 are attached.

As the shift lenses 15, five lenses having spherical degrees S2 of +10D, +5D, ±0D, −5D, and −10D, respectively, are prepared in advance. By combining one of the above lenses with the Alvarez lens 13, it is possible to set the synthetic spherical degree S (S1+S2) to one of the following ranges: −20D to ±0D, −15D to +5D, −10D to +10D, −5D to +15D, and ±0D to +20D. The range width of the spherical degree S of the Alvarez lens 13 is substantially enlarged to the range of −20D to +20D.

A pair of temple base portions 19a are pivoted to the side portions of the horizontal frame 19 of the main body 10. The temple base portions 19a are provided so as to be rotatable within a horizontal plane with respect to the horizontal frame 19.

Figure 3:
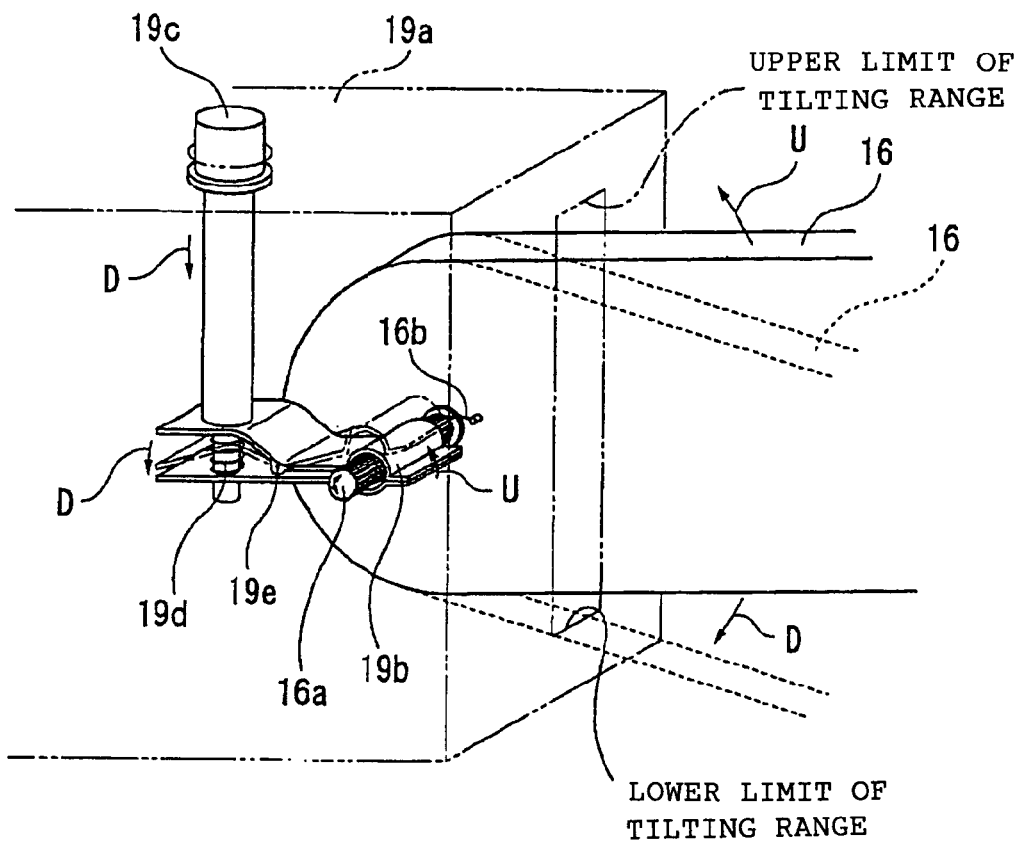
FIG. 3 is a main-portion see-through view of a temple lock mechanism.

As shown in FIG. 3, the above-mentioned temples 16 are pivoted to the temple base portions 19a so as to be capable of vertically tilting within a fixed angle range with respect to a horizontal plane so that they may allow adjustment to differences among individuals regarding the height of the ears of the subject 80, etc.

A lock mechanism is provided in each temple base portion 19a. To make it possible to effect switching with a single operation between an unlocked state in which the temple 16 can be tilted within the above tilting range and a locked state in which the temple 16 is fixed at a desired position within the tilting range, this lock mechanism is constructed as follows.

More specifically, as shown in FIG. 3, the lock mechanism includes a rotation shaft 16a, a lock member 19b, a push-button 19c, and a spring (biasing means) 19d. The rotation shaft 16a protrudes horizontally from the front side of the temple 16 and has a longitudinally extending groove. In the locked state, the lock member 19b is engaged with the groove of the rotation shaft 16a to prevent rotation of the rotation shaft 16a. In the unlocked state, the lock member 19b is detached from the groove of the rotation shaft 16a, and allows the rotation shaft 16 to rotate freely. The push-button 19c is used to switch the lock member 19b between the locked state and the unlocked state with one motion. The spring 19d urges-the push-button 19c such that the lock member 19b is held in the locked state.

When it is being biased by the spring 19d, the push-button 19c protrudes upwards from the upper surface of the temple base portion 19a.

The lock member 19b is adapted to undergo a see-saw-like rotational displacement around an axle 19e. When the push-button 19c, upwardly biased by the spring 19d, is depressed downwards as indicated by an arrow D against the biasing force, the lower portion of the push-button 19c presses one end portion of the lock member 19b (the left-hand end portion thereof as seen in FIG. 3) downwards. At this time, the other end portion of the lock member 19b (the right-hand end portion thereof as seen in FIG. 3) is raised upwards as indicated by an arrow U, using the axle 19e as the rotation center. Then, the engagement between the groove formed in the inner surface of the other end portion of the lock member 19b and the groove of the rotation shaft 16a is released to allow rotation of the rotation shaft 16a, whereby the temple 16, which is integral with the rotation shaft 16a, is brought into the state in which the temple 16 can be tilted in the vertical directions as indicated by the arrows U and D.

When, on the other hand, the depression of the push-button 19c is released, the push-button 19c is restored to its upper position as indicated by the arrow U by the biasing force of the spring 19, and the above-mentioned one end portion of the lock member 19b is restored to its former position. At the same time, the other end portion of the lock member spring 19 is displaced downwards as indicated by the arrow D, and the groove in the inner surface thereof and the groove of the rotation shaft 16a are engaged with each other again to thereby prevent rotation of the rotation shaft 16a. As a result, the temple 16 is fixed at the tilting position when the depression of the push-button 19d is released.

In the vicinity of the base of the rotation shaft 16a of the temple 16, there is arranged a helical spring 16b for imparting upward torque to the temple 16. Due to the helical spring 16b, it is possible to reduce the requisite force for displacing the temple 16 in the unlocked state upward as indicated by the arrow U.

Portions of the temples 16 which are put on the ears of the subject 80 have cutouts 16c. These cutouts 16c are formed so as to be relatively long in the longitudinal direction so that the temples 16 may be appropriately placed on the ears of the subject 80 regardless of the individual differences in terms of the longitudinal positions of the ears of the subject 80.

Further, connected to the rear end portions of the right and left temples 16 is a head band (Velcro strap) 16d connecting these temples 16 to each other. By wrapping this head band 16d around the back of the head of the subject 80, the main body 10 of the subjective optometric apparatus 100 is attached to the head of the subject 80.

The nose pad member 17 is mounted to the main body 10 through the intermediation of a support bar 17a extending through the horizontal frame 19. Further, the forehead rest member 18 is mounted to the main body 10 through the intermediation of support bars 18a and 18b extending through the horizontal frame 19.

Figure 4A:
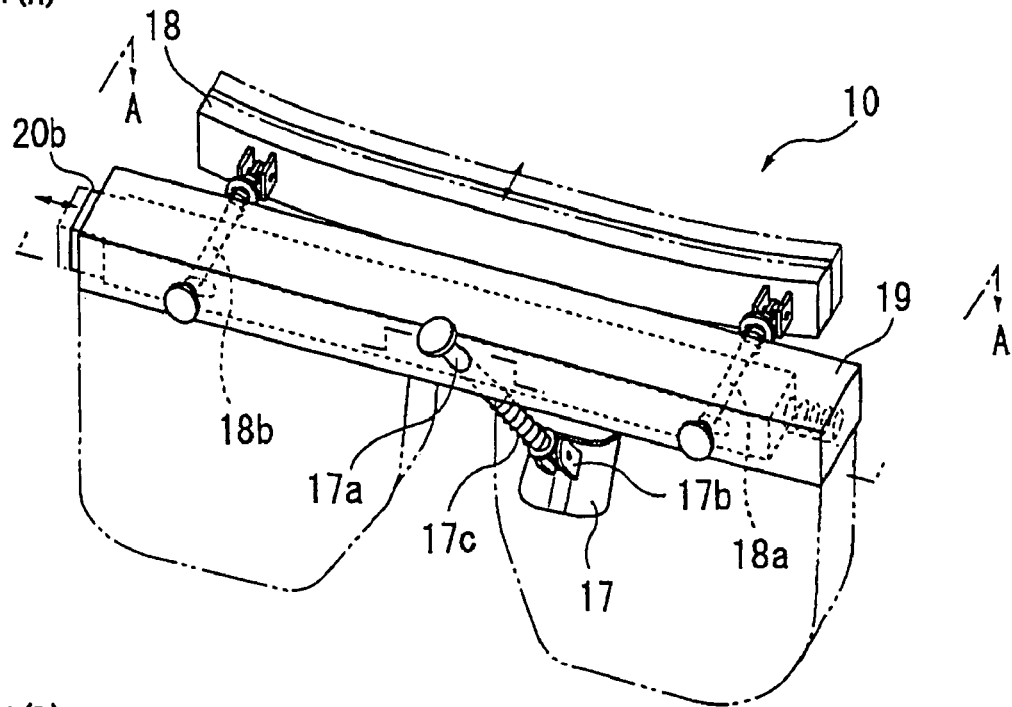
FIGS. 4A through 4C are a perspective view and sectional views illustrating how switching between locked state and unlocked state is effected on the nose pad member and the forehead rest member.
Figure 4B:
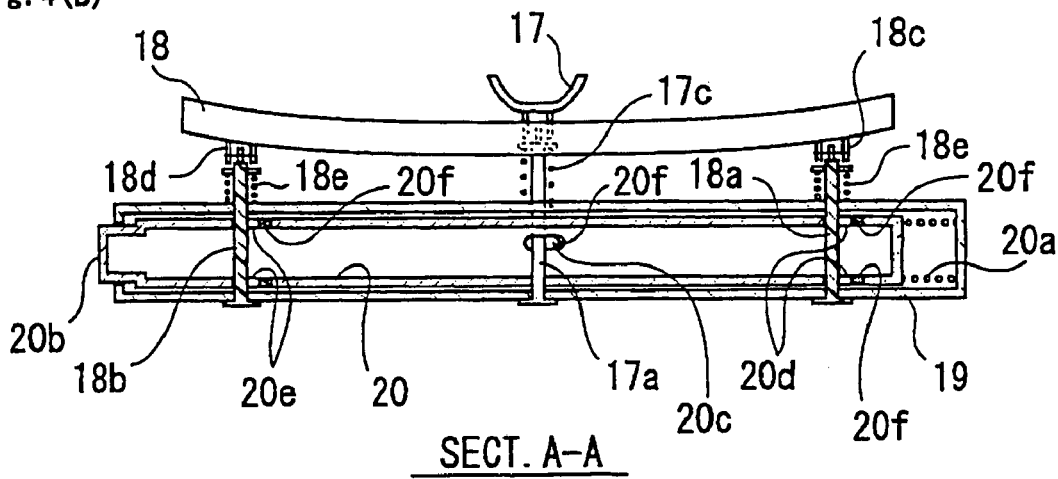
Figure 4C:
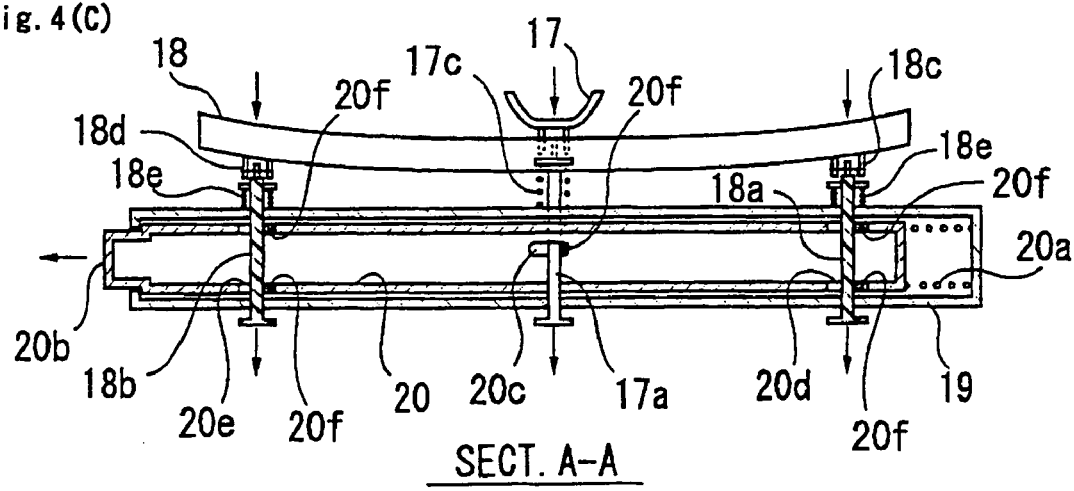

As shown in FIGS. 4A through 4C, the nose pad member 17 and the support bar 17a are connected together through the intermediation of a link member 17b allowing the nose pad member 17 to rotate within a vertical plane. Further, the forehead rest member 18 and the support bars 18a and 18b are connected together through the intermediation of link members 18c and 18d allowing the forehead rest member to rotate within a vertical plane.

As shown in FIGS. 4A through 4C, an inner tube 20 is inserted into the horizontal frame 19. Provided between the right-hand end outer wall of the inner tube 20 and the right-hand end inner wall of the horizontal frame 19 is a spring 20a biasing the inner tube 20 toward the left-hand side as seen in the drawings. The left-end portion of the inner tube 20, biased by the spring 20a, protrudes beyond the left-hand end of the horizontal frame 19 to form a push-button 20b.

Further, the inner tube 20 has, at positions substantially coinciding with the positions where the support bars 17a, 18a, and 18b pass through the horizontal frame 19, two through-holes 20c through which the support bar 17a is passed, two through-holes 20d through which the support bar 18a is passed, and two through-holes 20e through which the support bar 18b is passed.

The through-holes 20c, 20d, and 20e are formed as elongated holes extending in the longitudinal direction of the inner tube 20 so that the passing of the support bars 17a, 18a, and 18b is not hindered even if the inner tube 20 is displaced to the right against the biasing force of the spring 20a.

Further, rubber members 20f serving as anti-slip members are glued to the right-hand ends as seen in the drawings of the through-holes 20c, 20d, and 20e.

When the push-button 20b is pushed in to displace the inner tube 20 to the right in the drawings, the support bars 17a, 18a, and 18b are made movable in the direction in which they are passed through the horizontal frame 19 and the inner tube 20 (unlocked state). In contrast, in the state in which the inner tube 20 is being biased to the left by the spring 20a, the rubber members 20f of the through-holes 20c, 20d, and 20e are firmly pressed against the peripheral surfaces of the support bars 17a, 18a, and 18b, whereby movement of the support bars 17a, 18a, and 18b with respect to the horizontal frame 19 and the inner tube 20 is prevented (locked state).

On the portion of the support bar 17a between the link member 17b and the horizontal frame 19, there is arranged a spring 17c for biasing the nose pad member 17 toward the subject 80. Further, on the portion of the support bar 18a between the link member 18c and the horizontal frame 19, there is arranged a spring 18e for biasing the forehead rest member 18 toward the subject 18. Similarly, a spring 18e is also arranged on the support bar 18b.

Figure 5:
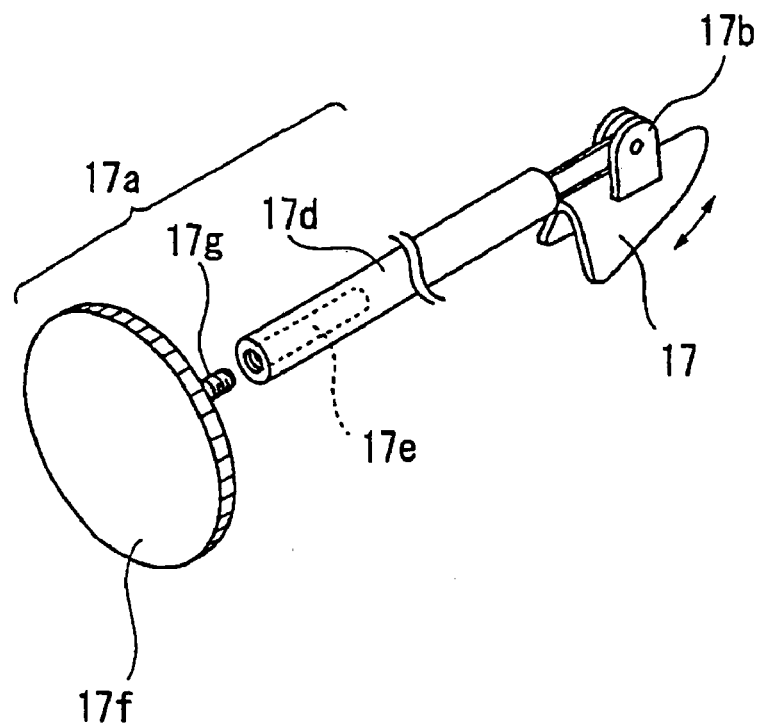
FIG. 5 is an explanatory exploded perspective view showing a support bar in a separated state.

As shown in FIG. 5, the support bar 17a supporting the nose pad member 17 can be separated into a cylindrical body portion 17d and a disc-like end portion 17f.

The body portion 17d and the end portion 17f are integrated into the support bar 17a through threaded engagement of a female screw 17e formed in the body portion 17d and a male screw 17g formed on the end portion 17f.

Due to the construction in which the support bar 17a can be separated into the body portion 17d and the end portion 17f, it is possible to detach the nose pad member 17 from the main body 10 for replacement or washing.

The support bars 18a and 18b supporting the forehead rest member 18 have a construction similar to that of the support bar 17a, making it possible for the forehead rest member 18 to be detached from the main body 10 for replacement or washing.

Next, the operation of the subjective optometric apparatus 100 of this embodiment will be described.

First, the oculist or the like holds the subjective optometric apparatus 100 with both hands, directing it toward the subject 80. At this time, the oculist or the like holds the right and left temple base portions 19a with his right and left hands, respectively, depressing the push-button 19c of each temple base portion 19a with a finger of each hand (e.g., the first finger). At the same time, he maintains a state, with another finger of his left hand (e.g., the second finger), in which the push-button 20b of the horizontal frame 19 is pushed in to the right.

As described above, by pressing downwards the push-buttons 19c of the temple base portions 19a, the temples 16 become capable of tilting vertically as indicated by the arrows U and D.

Further, by pushing in the push-button 20b of the horizontal frame 19, the support bars 17a, 18a, and 18b are released from the frictional force of the rubber members 20f of the through-holes 20c, 20d, and 20e. Then, the support bar 17a is moved by the spring 17c, and the nose pad member 17 is biased toward the subject 80. Further, the support bars 18a and 18b are moved by the springs 18e, and the forehead rest member 18 is biased toward the subject 80.

The right and left temples 16, which have become capable of tilting, tilt downwardly due to their own weight.

Figure 6A:
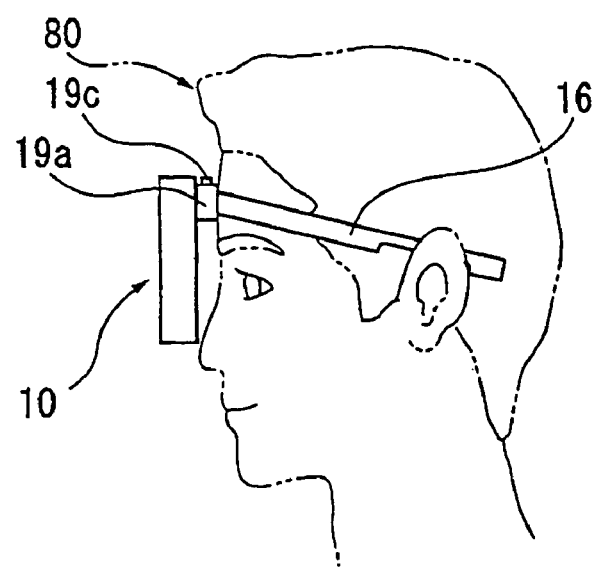
FIGS. 6A through 6C are schematic diagrams illustrating the temple movement when the subject puts on the main body of the device.

In this state, as shown in FIG. 6A, the oculist or the like puts the main body 10 on the face of the subject 80 from above while maintaining the temples 16 in the tiltable state by keeping the push-buttons 19c depressed.

At this time, the rear end portions of the downwardly tilted temples 16 are placed on the ears of the subject 80 (FIG. 6A). Then, the main body 10 is lowered slowly while keeping the push-buttons 19c pressed downwords, until the positions of the eyes of the subject 80 are matched with the height of the optometric windows 11a and 12a.

All this while, the temples 16 are tiltable with respect to the main body 10, so that it is possible to lower the main body 10, with the temples 16 remaining on the ears of the subject 80.

Figure 6B:
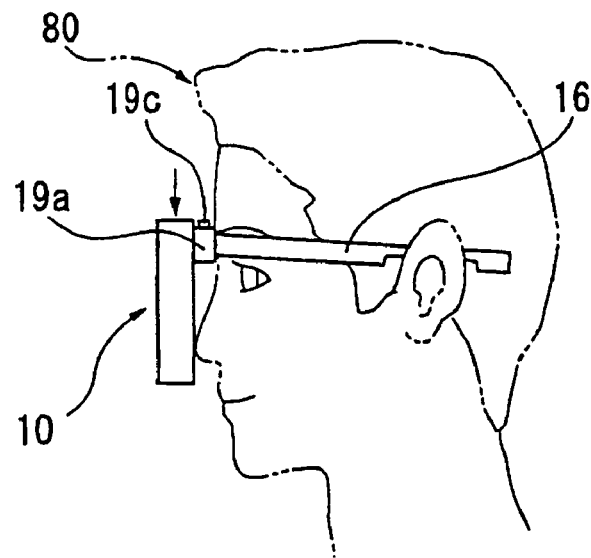
Figure 6C:
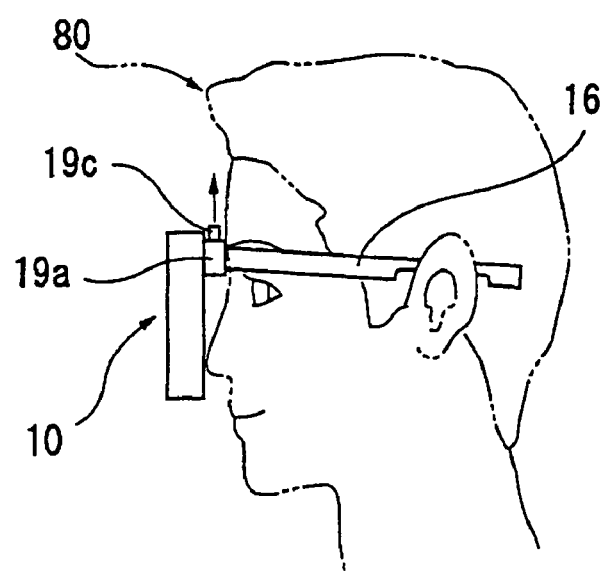

When the eye positions are matched with the height of the optometric windows 11a and 12a (FIG. 6B), the oculist or the like removes his fingers from the push-buttons 19c (FIG. 6C).

By the operation of removing the fingers from the push-button 19c, the temples 16 are fixed at the tilting positions where the eye positions are matched with the height of the optometric windows 11a and 12a.

Thus, the temples 16 are secured in position in a state in which they are properly placed on the ears of the subject 80. It is to be noted, in particular, that even in a case in which the heights of the right and left eyes differ from each other, it is possible for the main body 10 to be attached properly in conformity with such difference.

All this while, the push-button 20b of the horizontal frame 19 remains pushed in, so that the forehead rest member 18 can be freely displaced forwards and backwards (i.e., in the direction in which the support bars 18a and 18b are passed) in conformity with the configuration of the forehead while being kept in contact with the forehead of the subject 80 by the biasing force of the springs 18e.

Similarly, the nose pad member 17 can be freely displaced in an oblique direction (i.e., in the direction in which the support bar 17a is passed) in conformity with the configuration of the nose while being kept in contact with the nose of the subject 80 by the biasing force of the spring 17c.

Next, the oculist or the like removes his finger from the push-button 20b of the horizontal frame 19. Then, the rubber members 20f of the through-holes 20c, 20d, and 20e of the inner tube 20 are firmly pressed against the support bars 17a, 18a, and 18b to place the device in the locked state.

In this way, the nose pad member 17 is secured in position while in proper contact with the nose of the subject 80, and the forehead rest member 18 is secured in position while in proper contact with the forehead of the subject 80.

Thus, an improvement is achieved in terms of the intimacy with which the main body 10 is held in contact with the face of the subject 80, thereby making it possible to prevent the main body 10 from slipping down the face, i.e., moving relative to the face during optometry.

In this way, in the subjective optometric apparatus 100 of this embodiment, which uses the Alvarez lens 13 instead of the conventional turret type lens group, it is possible to substantially reduce the size and weight of the main body 10. Further, due to the provision of the temples 16, the nose pad member 17, and the forehead rest member 18, it is possible to attach the main body 10 directly to the face of the subject 80 like a trial frame.

Further, it is possible to attach the main body 10 to the face of the subject 80 properly solely through the simple operation of releasing the push-buttons 19c and 20b from the pushed-in state.

Thus, it is possible to perform fitting for each subject 80 by a simple operation and in a very short time, so that the burden on the oculist or the like is relieved, and the subject 80 suffers no excessive stress.

Further, it is also possible to adopt an arrangement in which a synthetic spherical degree S (as mentioned above) is automatically obtained on the basis of the spherical degree of the Alvarez lens 13 and the spherical degree of the shift lenses 15 to thereby relieve the inspection burden on the operator and achieve an improvement in inspection accuracy.

For example, there is provided a detecting means for detecting the relative vertical displacement amount of the optical elements 13a and 13b of the Alvarez lens 13, and there are provided, in the tab portions 15a or the like of the shift lenses 15, reflection patterns for optically identifying the shift lenses 15 and photo detectors for optically reading the reflection patterns. The spherical degree of the Alvarez lens 13 is obtained from the displacement amount of the optical elements 13a and 13b detected by the detecting means, and the spherical degrees of the shift lenses 15 are identified from the reflection patterns detected by the photo detectors, computation for synthesizing these spherical degrees being executed to automatically obtain a synthetic spherical degree S.

As the detecting means for the Alvarez lens 13, it is possible, for example, to adopt the following construction. First, by using a motor and a rack-and-pinion gear for converting rotation of this motor to vertical displacement, the optical elements 13a and 13b are caused to make a relative vertical movement. By detecting the amount of displacement of the rack-and-pinion gear from a reference position by an encoder, such as a rotary encoder or a linear encoder, it is possible to detect the relative vertical displacement of the optical elements 13a and 13b corresponding to the above displacement amount.

When obtaining the spherical degree from the detection result obtained by the detecting means, a table or the like is referred to in which the displacement amount of the rack-and-pinion gear. (the relative displacement amount of the optical elements 13a and 13b) and the spherical degree the Alvarez lens exhibits are related to each other. Further, also when obtaining the spherical degree from the detection result obtained by the photo detector, a table or the like is similarly referred to in which the pattern configuration of the reflection patterns and the spherical degree of the shift lenses 15 are related to each other.

In identifying the shift lenses 15, it is possible, apart from the above optical method, to appropriately adopt an electrical method, a magnetic method, a mechanical method, etc. As for an electrical method, it is possible, for example, to provide the tab portions 15a, etc. with electrical contacts with patterns differing according to the spherical degrees of the shift lenses 15, and to provide a detector for electrically reading the patterns of the electrical contacts. As an example of a magnetic method, the tab portions 15a, etc. are provided with magnetic contacts of a pattern differing according to the spherical degrees of the shift lenses 15, and a detector for magnetically reading the patterns of the magnetic contacts may be provided. As a mechanical method, the tab portions 15a are adapted to have different configurations according to the spherical degrees of the shift lenses 15, and there is provided a detector for reading the difference in configuration mechanically, electrically, magnetically, or optically.

Further, it is also possible to separately provide a display device, such as a monitor, for indicating various items of data, such as the spherical degree of the Alvarez lens 13 as detected by the detecting means, the spherical degrees of the shift lenses 15 as identified by the photo detectors, or the synthetic spherical degree thereof, and, further, the refraction characteristics of the Vcc lens 14, such as the cylindrical degree and the axial angle of the cylindrical axis. Further, it is also possible to provide a controller for controlling the various portions of the device while referring to the data as displayed on the display device, thereby achieving an improvement in operability.

[Modification]

In the subjective optometric apparatus 100 of the above-described embodiment, the switching of the temples 16 between the locked and unlocked states, and the switching of the nose pad member 17 and the forehead rest member 18 between the locked and unlocked states, are effected by separate push-buttons 19c and 20b. However, the subjective optometric apparatus of the present invention is not restricted to this form. It is also possible, for example, to adopt a construction in which the switching of the temples 16, the nose pad member 17, and the forehead rest member 18 between the locked and unlocked states is effected by a single lock mechanism (push-button or the like). Further, it is also possible to adopt a construction in which only the operations of switching between the locked and unlocked states for the temples 16 and the forehead rest member 18 are united so as to be effected with a single lock mechanism.

Figure 7:
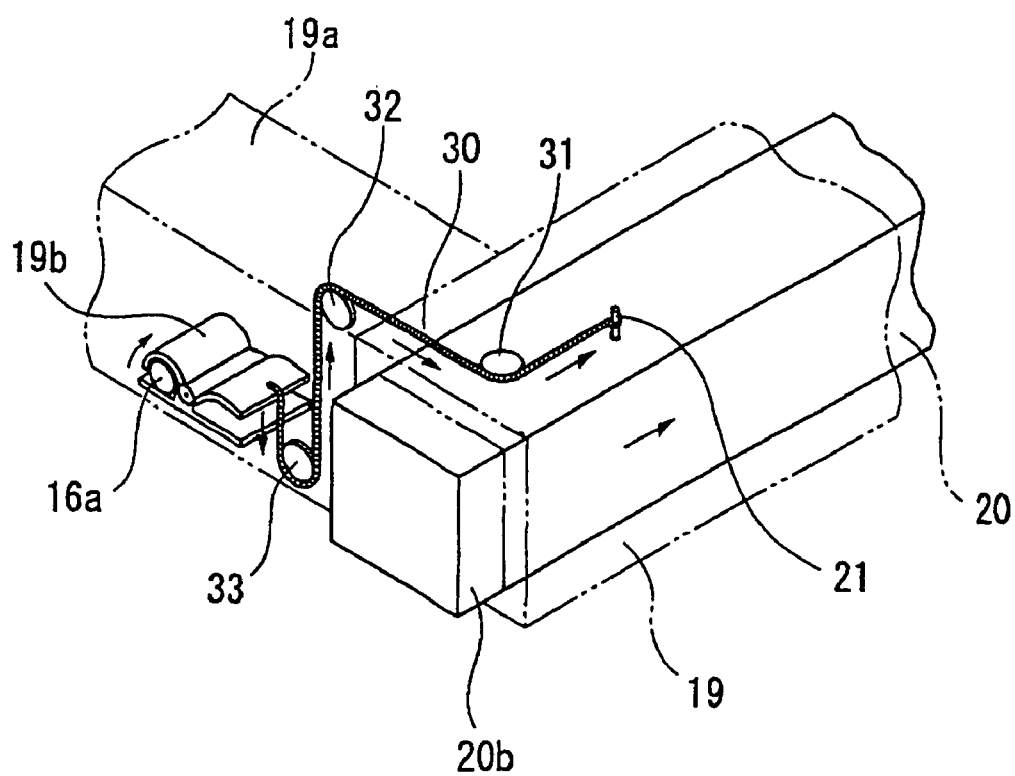
FIG. 7 is a main-portion see-through view showing an example of how operational connection between switching operations on a plurality of members is realized by a single push-button.

FIG. 7 is a main-portion see-through view showing an example of a construction in which the switching between the locked and unlocked states for the temples 16, the nose pad member 17, and the forehead rest member 18 is effected with a single push-button 20b. In the construction shown, the movement of the push-button 20b shown in FIG. 4 and the movement of the lock member 19b shown in FIG. 3 are operationally connected. In the construction shown in FIG. 7, the push-button 20b and the lock member 19b are connected by a flexible wire 30 wrapped around a pulley 31 rotatably supported by a horizontal frame 20 and around pulleys 32 and 33 rotatably supported by a temple base portion 19a.

In this construction, when the push-button 20b is pushed in as indicated by the arrow, the nose pad member 17 and the forehead rest member 18 are unlocked. Further, the wire 30, one end of which is connected to a pin 21 provided on the inner tube 20, is displaced in the direction of the arrow, and the lock member 19b of the temple 16, which is connected to the other end of the wire 30, is unlocked. When the push-button 20b is restored to the former position, the nose pad member 17, the forehead rest member 18, and the temples 16 are locked through an operation reverse to the above.

Thus, solely by operating a single push-button 20b (lock mechanism), switching between the locked and unlocked states can be effected on the temples 16, the nose pad member 17, and the forehead rest member 18, whereby a further improvement is achieved in terms of operability.

In the case in which switching between the locked and unlocked states is effected on a plurality of members by a single lock mechanism, the switching may be effected simultaneously on the members, or may be effected with appropriately different timings as needed.

To effect the switching with different timings, it is possible, for example, to make the thickness of the rubber members 20f provided in the through-holes 20c of the inner tube 20 different from that of the rubber members 20f provided in the through-holes 20d and 20e. Due to this arrangement, there is a difference between the timing with which the rubber members 20f of the through-holes 20c abut the support bar 17a of the nose pad member 17 and the timing with which the rubber members 20f of the through-holes 20d and 20e abut the support bars 18a and 18b of the forehead rest member 18, so that it is possible to effect switching on the nose pad member 17 and the forehead rest member 18 with different timings.

[Second Embodiment]

While the subjective optometric apparatus of the first embodiment described in detail above is worn by the subject and is completely unrestrained from outside, the subjective optometric apparatus of the present invention is not restricted to this form. In the following, another embodiment of the present invention will be described.

Figure 8:
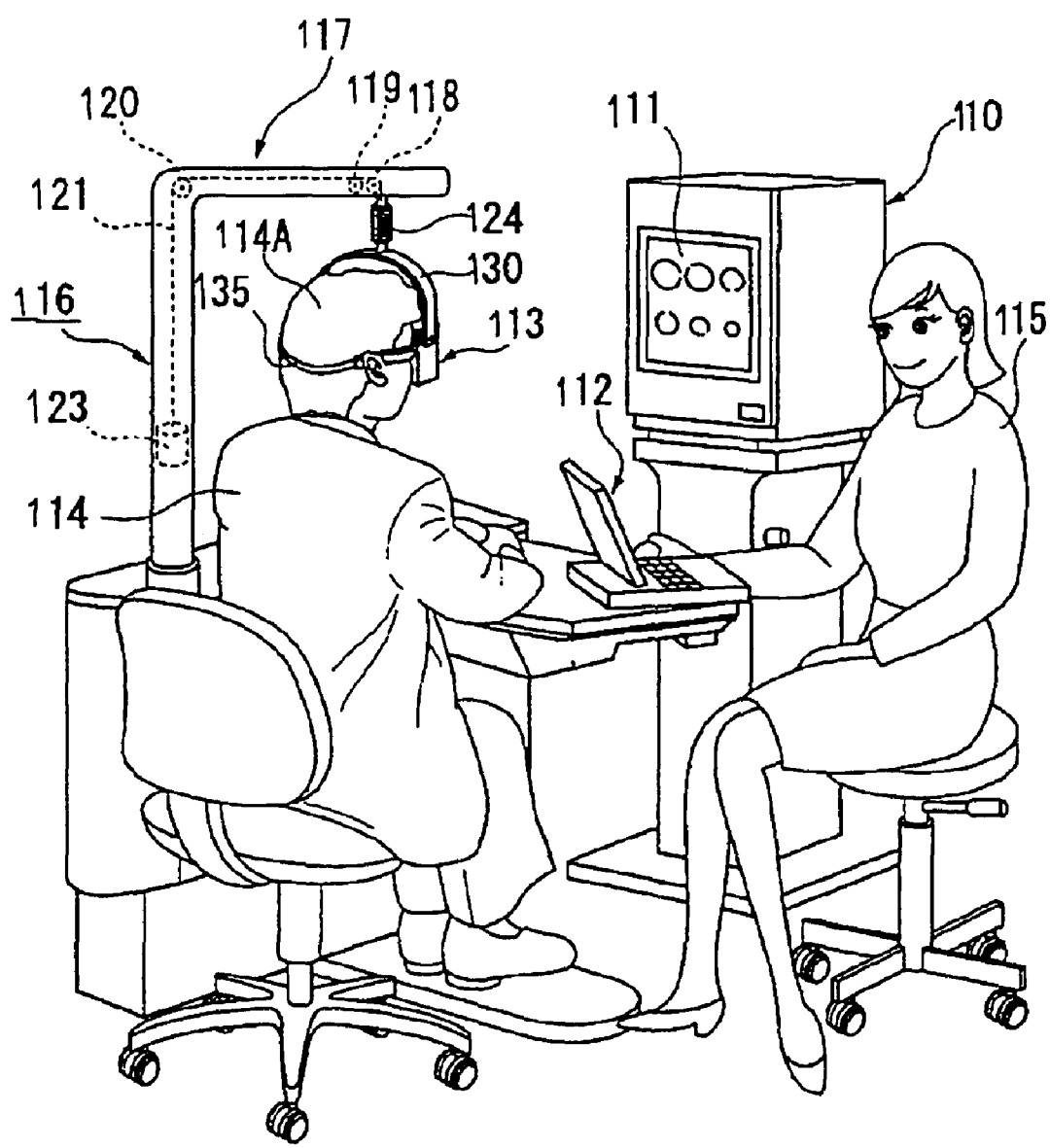
FIG. 8 is a schematic diagram showing the way a subjective optometric apparatus according to the present invention is used.

FIG. 8 schematically shows an optometric system using a subjective optometric apparatus according to the present invention. In the drawing, numeral 110 indicates a target presenting device, numeral 111 indicates a target, numeral 112 indicates a controller, numeral 113 indicates a subjective optometric apparatus (refractor head), numeral 114 indicates a subject, numeral 115 indicates an examiner, and numeral 116 indicates a post as a support portion.

Figure 9:
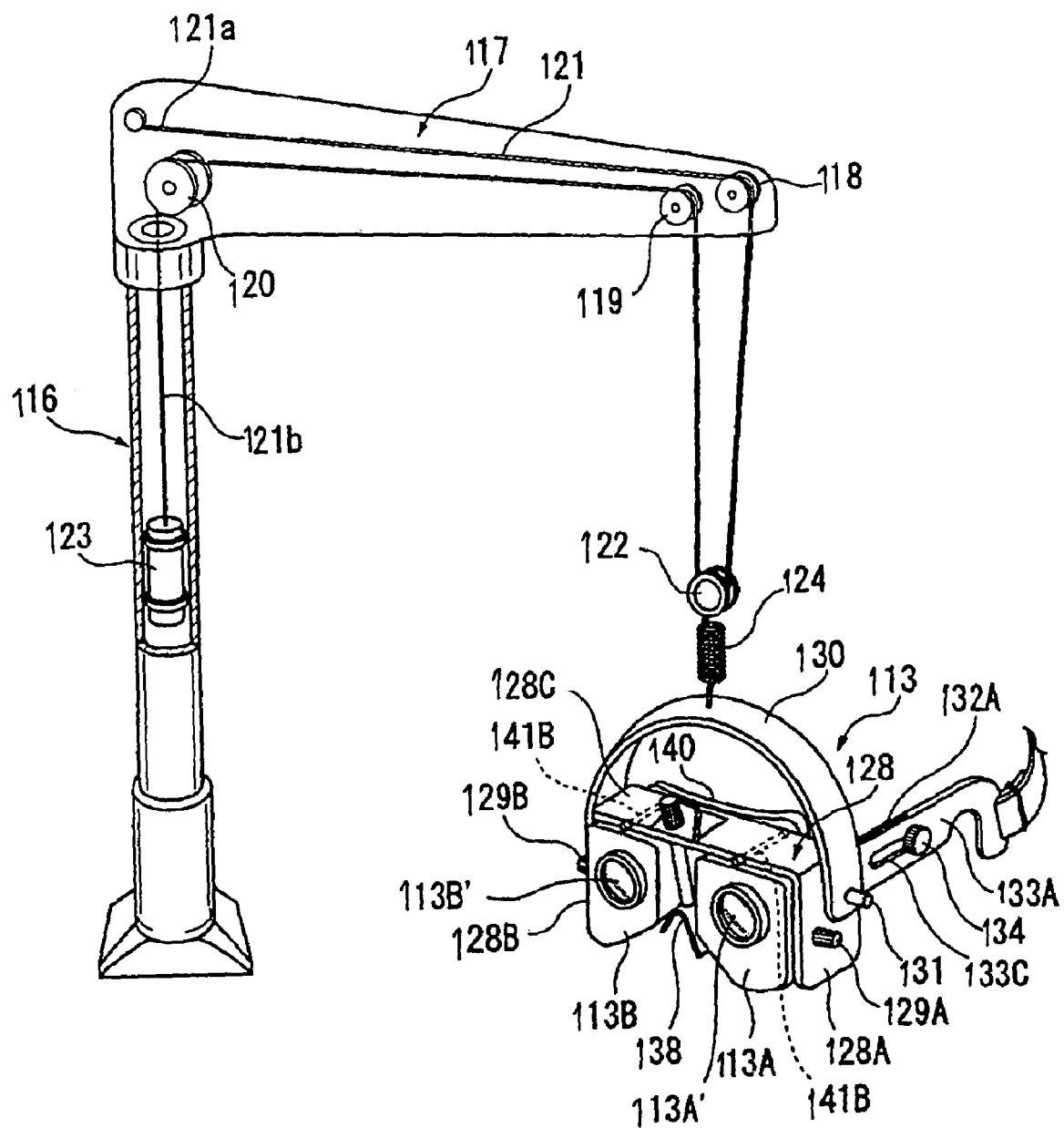
FIG. 9 is an enlarged perspective view of a main portion of a subjective optometric apparatus according to the present invention.

The post 116 is equipped with an arm 117. As shown in FIG. 9, which is an enlarged view, this arm 117 is equipped with pulleys 118 through 120. Further, a wire 121 is provided in the arm 117. This wire 121, one end portion 121a of which is fixed to the arm 117, is passed around the pulleys 118, 122, 119, and 120, and the other end portion 121b thereof is guided into the post 116. A balancing counter-weight 123 is mounted to the other end portion 121b of this wire 121. Further, the pulley 122 is equipped with a spring member 124.

Figure 10:
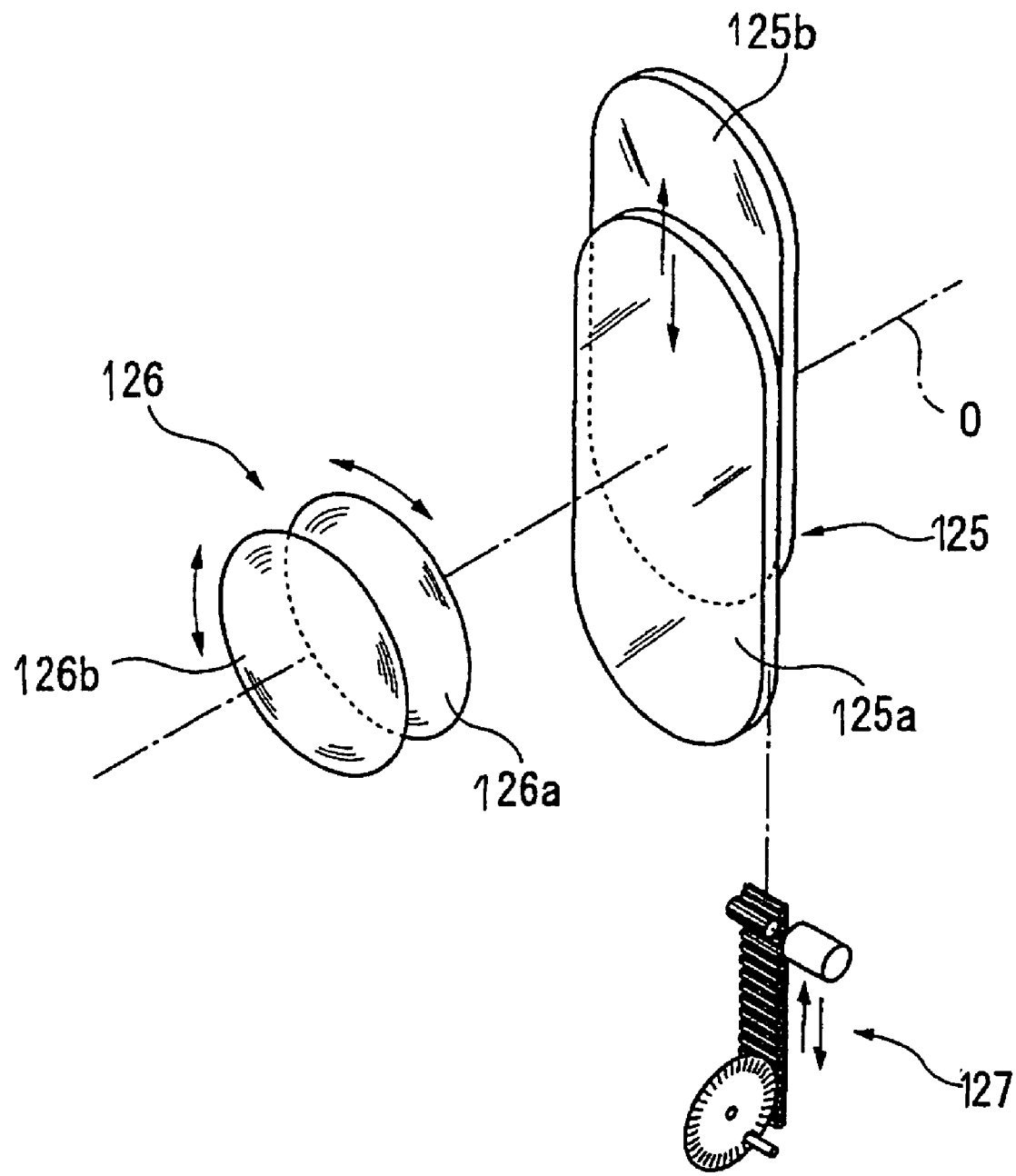
FIG. 10 is an optical diagram showing an example of the internal structure of the optometric unit shown in FIG. 9.

The subjective optometric apparatus 113 has a left-eye examination unit 113A and a right-eye examination unit 113B. The left-eye examination unit 113A and the right-eye examination unit 113B have optometric windows 113A' and 113B', respectively. Further, each of the left-eye examination unit 113A and the right-eye examination unit 113B is equipped with an Alvarez lens 125 and a Vcc lens 126 as shown in FIG. 10. The Alvarez lens 125 is composed of a pair of transparent optical elements 125a and 125b, such as phase plates. The Vcc lens 126 is composed of two cylindrical lenses 126a and 126b. The Alvarez lens 125 and the Vcc lens 126 are arranged coaxially with the optical axis 0 of the optometric window 113A', 113B'.

Inside each of the left-eye examination unit 113A and the right-eye examination unit 113B, there is provided a displacement drive mechanism 127 for causing the optical elements 125a and 125b to make relative displacement vertically and horizontally. This displacement drive mechanism 127 is composed, for example, of a rack and pinion, a drive motor, and a control circuit. In FIG. 10, the displacement drive mechanism for causing the optical elements 125a and 125b to make relative displacement in the horizontal direction is not shown.

Further, in each of the left-eye examination unit 113A and the right-eye examination unit 113B, there is provided a rotation drive mechanism (not shown) for rotating the cylindrical lenses 126a and 126b. The controller 112 and the subjective optometric apparatus 113 are electrically connected to each other, and the displacement drive mechanism 127 and the rotation drive mechanism are controlled by the controller 112.

As shown in FIG. 9, the left-eye examination unit 113A and the right-eye examination unit 113B are retained by a retaining frame member 128 in a U-shaped configuration serving as a support member. This retaining frame member 128 has side plate portions 128A and 128B and a top plate portion 128C. In the lower surface of the top plate portion 128C, there is formed a guide groove (not shown) extending from the side plate portion 128A to the side plate portion 128B.

In each of the left-eye examination unit 113A and the right-eye examination unit 113B, there is formed an engagement portion (not shown) to be engaged with the above-mentioned guide groove of the retaining frame member 128. Provided on the side plate portion 128A is a movement adjustment knob member 129A for moving the left-eye examination unit 113A along the guide groove. Also provided on the side plate portion 128B is a movement adjustment knob member 129B for moving the right-eye examination unit 113B along the guide groove. By adjusting the movement adjustment knob members 129A and 129B, the left-eye examination unit 113A and the right-eye examination unit 113B are moved toward and away from each other along the above-mentioned guide groove, whereby the positions of units 113A and 113B in accordance with the interpupillary distance PD of the subject 114 are adjusted.

An arcuate support arm 130 bridges the side plate portions 128A and 128B of the support frame member 128 so as to be rotatable around axles 131. The subjective optometric apparatus 113 is longitudinally rotatable around the axles 131 with respect to the arcuate support arm 130. A coil spring 124 is hooked onto the top portion of the arcuate support arm 130. While in this example the arcuate support arm 130 is rotatable with respect to the retaining frame member 128, it is also possible for the arcuate support arm 130 to be fixed to the retaining frame member 128.

Figure 11:
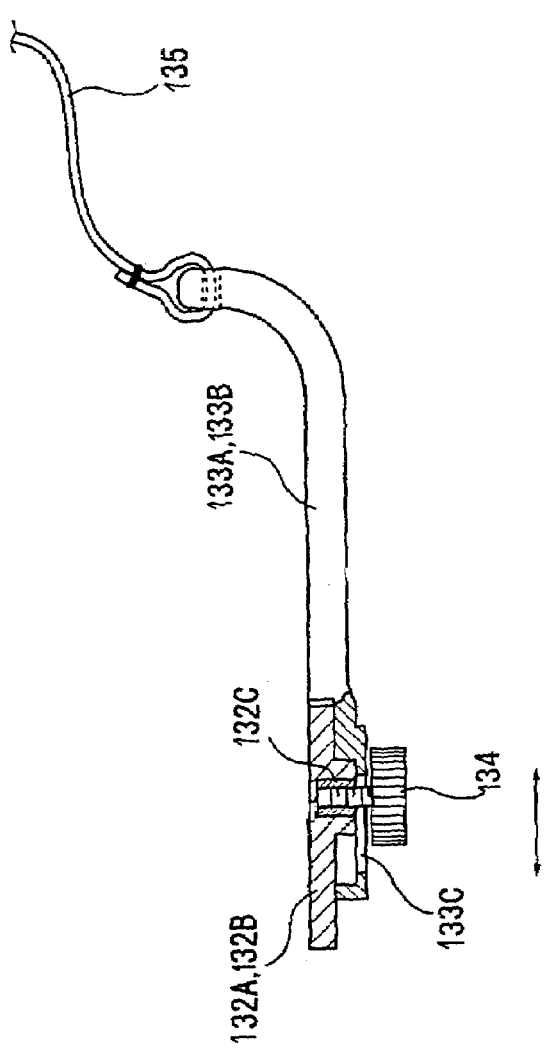
FIG. 11 is a partial sectional view of an example of an earpiece member as an attachment member.
Figure 12:
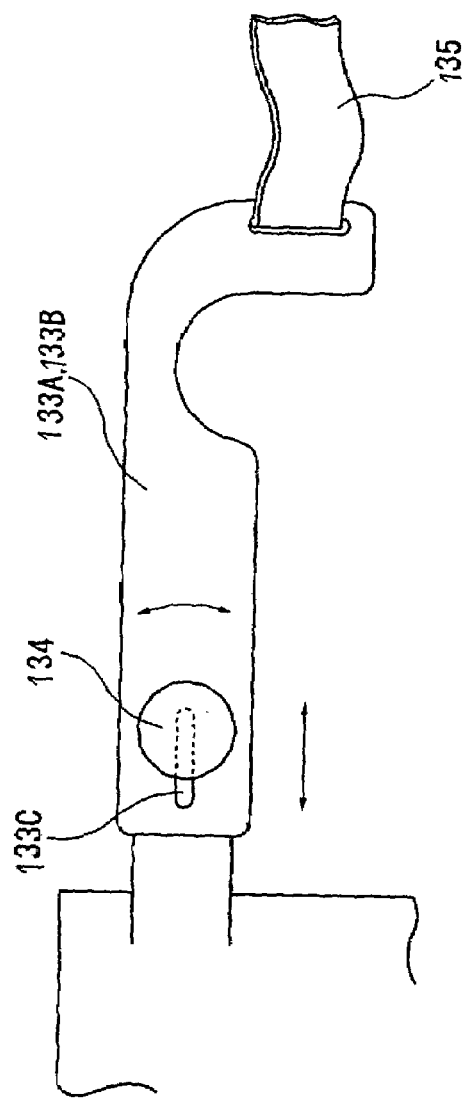
FIG. 12 is a partial sectional view of the earpiece member shown in FIG. 11.
Figure 13:
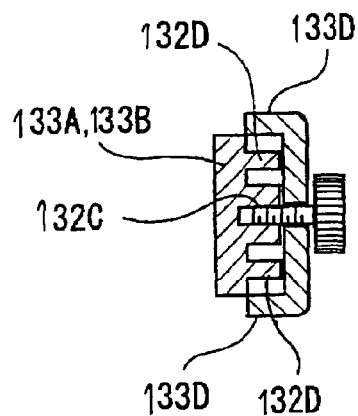
FIG. 13 is a longitudinal sectional view of a fastening portion of the earpiece member shown in FIG. 11.

The side plate portions 128A and 128B of the retaining frame member 128 are respectively equipped with guide plates 132A and 132B as shown in FIG. 11. Further, as shown in FIGS. 12 and 13, connected to the guide plates 132A and 132B are earpiece members 133A and 133B serving as the attachment members provided so as to be slidable in the direction in which they extend. Further, each of the guide plates 132A and 132B is equipped with a screw hole 132C to be threadedly engaged with a cap screw 134. Each of the earpiece members 133A and 133B is equipped with an elongated hole 133C extending in the direction in which it slides. Each of the guide plates 132A and 132B is equipped with a tilting angle regulating protrusion 132D. Further, formed on each of the earpiece members 133A and 133B is an engagement portion 133D to be engaged with the tilting angle regulating protrusion 132D.

The adjustment of the length of the earpiece members 133A and 133B and the adjustment of the tilting angle thereof are effected by loosening the cap screws 134, allowing the earpiece members 133A and 133B to slide, and fastening them at positions where they are fit by the cap screws 134.

Figure 14:
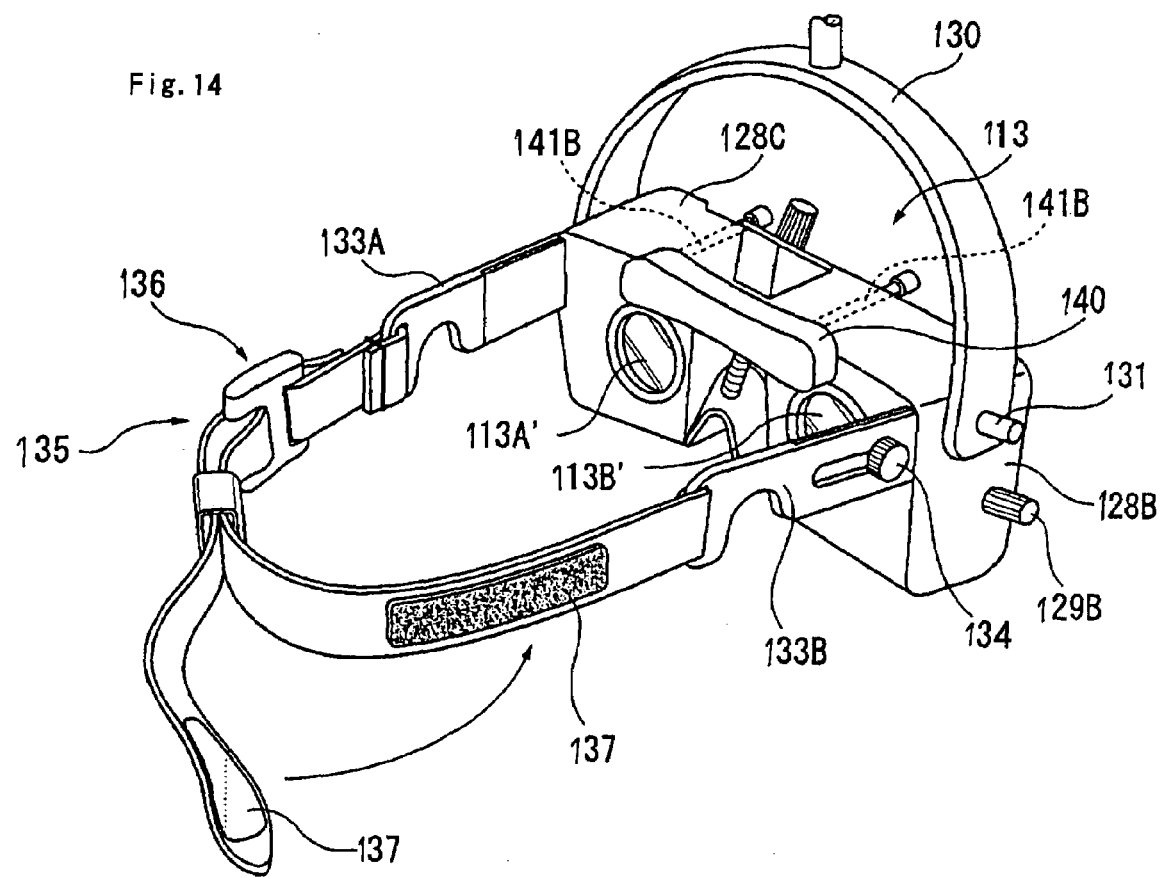
FIG. 14 is a perspective view as seen from the rear side, of the subjective optometric apparatus shown in FIG. 9.

An attachment belt 135 is provided at the rear ends of the earpiece members 133A and 133B. Due to a buckle mechanism 136 as shown in FIG. 14, the attachment belt 135 allows adjustment of the force with which the device is fastened to the head 114A of the subject 114. Further, there is also provided a lock member 137 (consisting, for example, of Magic Tape (registered trademark)) for locking the forward end portion of the attachment belt 135.

Figure 15:
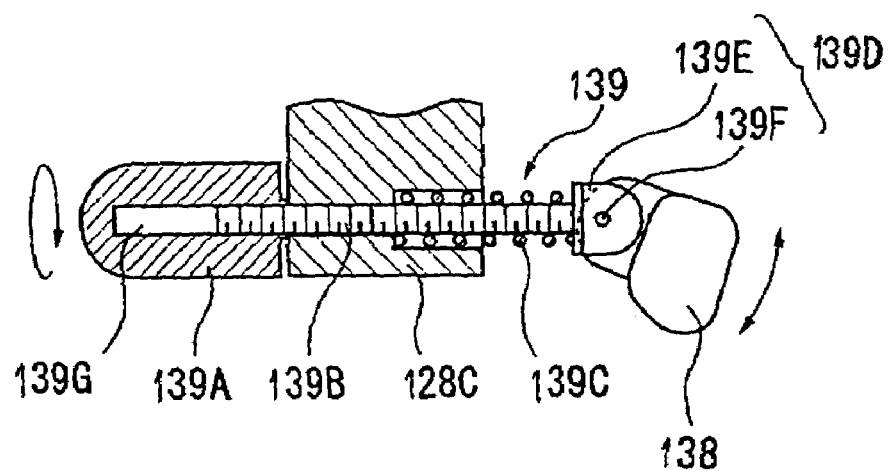
FIG. 15 is a partial sectional view of an example of the nose pad member adjusting mechanism shown in FIG. 2.

At the center of the top plate portion 128C of the retaining frame member 128, there is provided a nose pad member 138. The nose pad member 138 is adjusted in position by an adjusting mechanism 139 so that it may fit the nose. As shown in FIG. 15, the adjusting mechanism 139 is substantially composed of an adjusting knob member 139A, an adjusting rod 139B, an biasing spring 139C, and a swinging mechanism 139D. The adjusting rod 139B is passed obliquely downwards from above through the top plate portion 128C. At the forward end of the adjusting rod 139B, there are provided a pair of brackets 139E forming the swinging mechanism 139D. A rotation shaft 139F bridges the brackets 139E. The nose pad member 138 is supported so as to be rotatable around this rotation shaft 139F.

The adjusting knob member 139A is provided at the rear end of the adjusting rod 139B. This adjusting knob member 139A is equipped with a screw hole 139G. Further, the outer periphery of the adjusting rod 139B is threaded. Between the lower portion of the top plate portion 128C and the brackets 139E, there is provided a biasing spring 139C for adjusting the pressurizing force applied to the nose.

Figure 16:
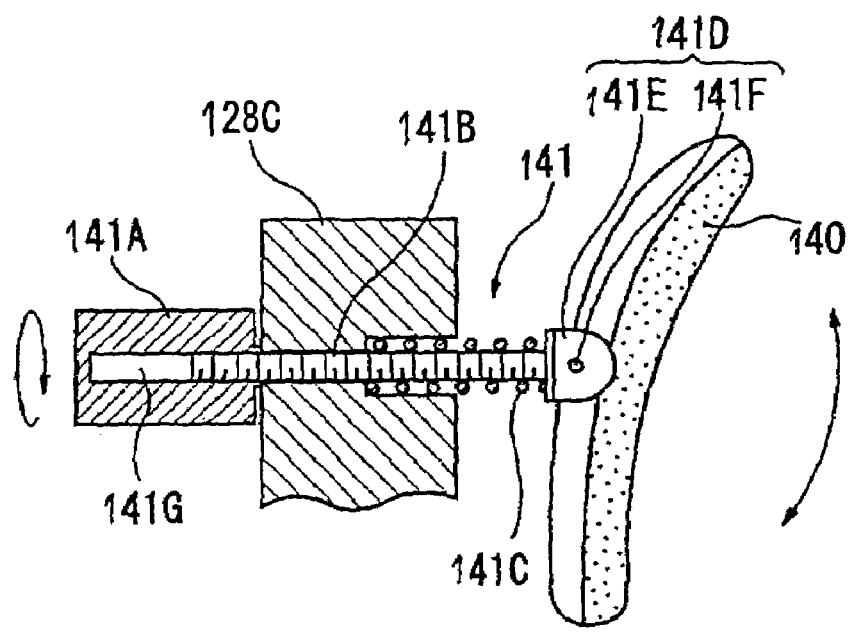
FIG. 16 is a partial sectional view of an example of the forehead rest adjusting mechanism shown in FIG. 2.

Further, as shown in FIG. 16, the top plate portion 128C is equipped with a forehead rest 140. This forehead rest 140 is adjusted in position by a (forehead rest) adjusting mechanism 141 so as to fit the forehead of the subject 114. The adjusting mechanism 141 is substantially composed of an adjusting knob member 141A, adjusting rods 141B, biasing springs 141C, and swinging mechanisms 141D. As shown in FIG. 14, there are provided right and left adjusting rods 141B, which longitudinally pass through the top plate portion 128C. At the forward end of each adjusting rod 141B, there are provided a pair of brackets 141E constituting the swinging mechanism 141D. A rotation shaft 141F bridges the brackets 141E. The forehead rest 141 is supported so as to be rotatable around the rotation shaft 141F. The adjusting knob member 141A is equipped with a screw hole 141G. Further, the outer periphery of each adjusting rod 141B is threaded. Between the top plate portion 128C and the brackets 141E, there are provided biasing springs 141C for adjusting the pressurizing force with which the forehead rest 141 is applied to the forehead.

Due to the above—described construction, the weight of the subjective optometric apparatus 113 is balanced by the balancing counterweight 123. Thus, if the subject 114 shakes his head with the subjective optometric apparatus 113 on, he does not practically perceive the weight of the device, thus relieving the burden on the subject 114. Further, if the subject nods his head, the subjective optometric apparatus 113 follows the nodding movement, so that the burden on the subject 114 is relieved.

The above-described embodiments should not be construed restrictively. It is also possible to adopt the following constructions.

[Modification 1]

Figure 17:
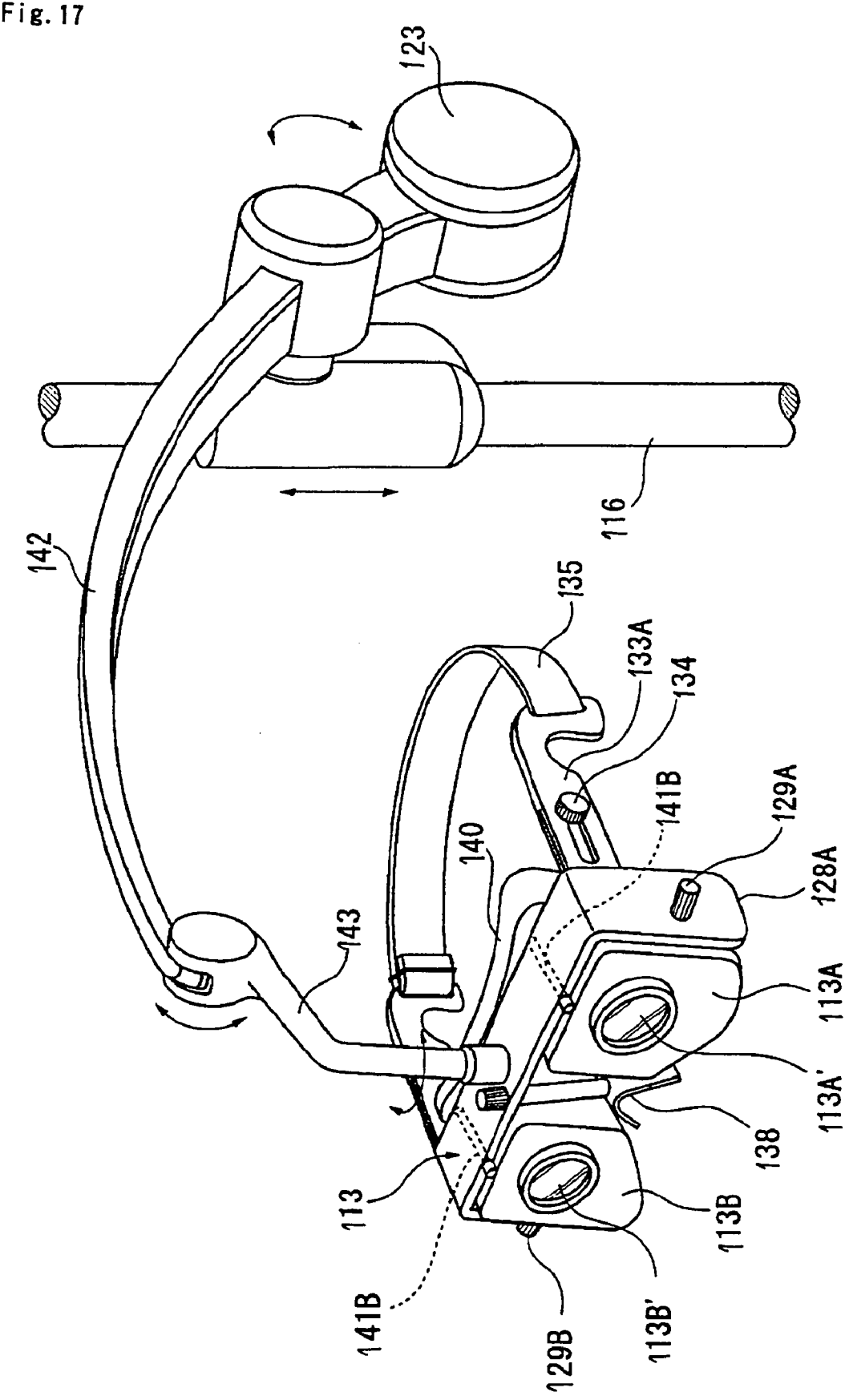
FIG. 17 is a perspective view of a modification of the subjective optometric apparatus of the present invention.

In the first modification shown in FIG. 17, an arcuate arm member 142 allowing vertical adjustment is provided on the post 116. At the forward end of this arcuate arm member 142, there is provided a vertically rotatable suspension arm member 142. Further, at the lower end of the suspension arm member 143, a subjective optometric apparatus 113 is provided so as to be horizontally rotatable. Further, at the rear end of the arcuate arm member 142, there is provided a balancing counter 123 for balancing the weight of the subjective optometric apparatus 113.

[Modification 2]

Figure 18:
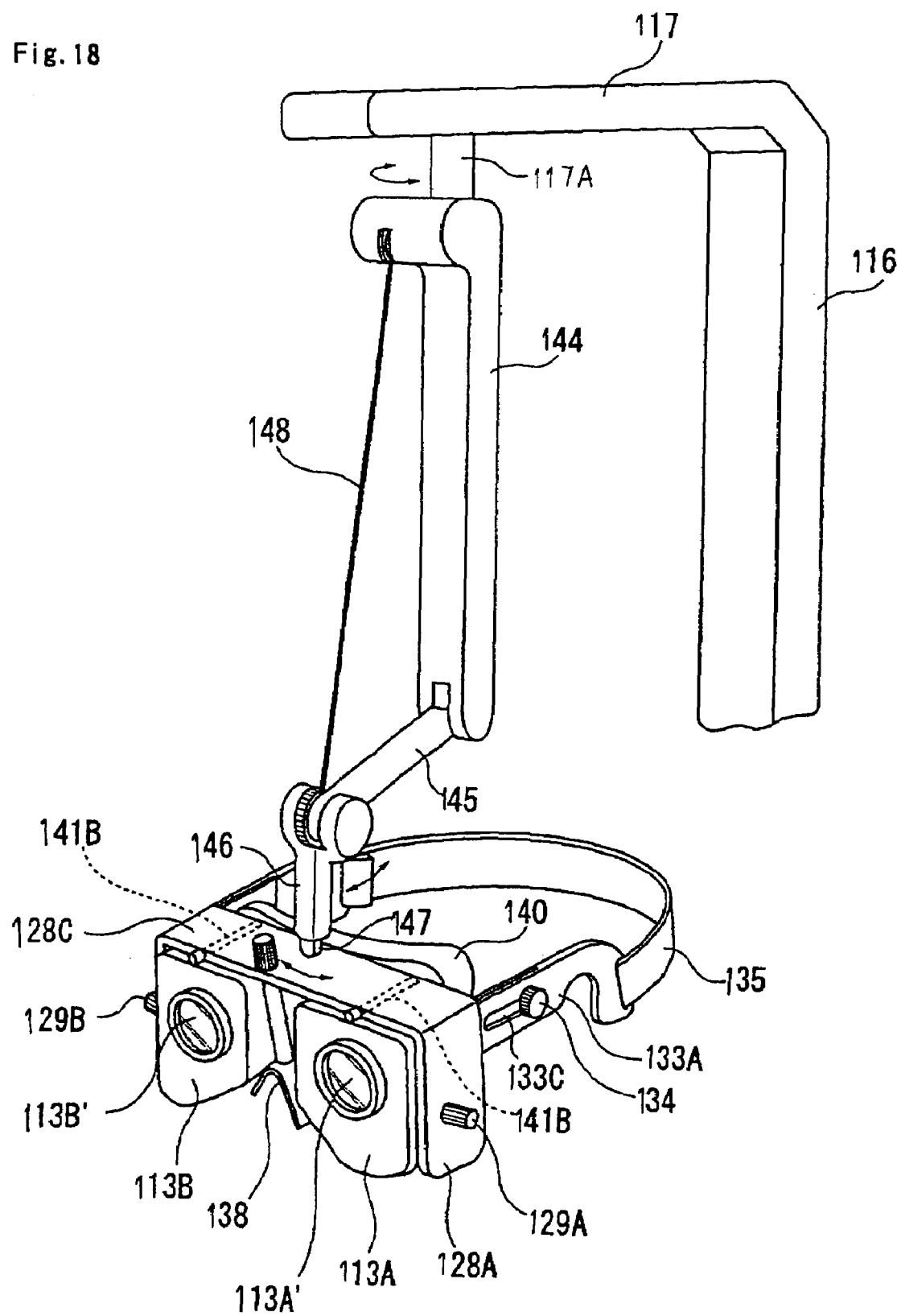
FIG. 18 is a perspective view of another modification of the subjective optometric apparatus of the present invention.

In the second modification shown in FIG. 18, the arm 117 of the post 116 is equipped with a rotation shaft 117A, and at the lower end of this rotation shaft 117A, there is provided a horizontally rotatable first arm 144. The first arm 144 is equipped with a second arm 145 on whose one end the second arm 145 is vertically rotatable. A third arm 146 is connected to the other end of the second arm 145 so as to be longitudinally rotatable. The subjective optometric apparatus 113 is connected to a horizontal rotation shaft 147 of the third arm 146. Further, the other end of the second arm 145 is suspended from the first arm 144 by a coil spring type wire 148. In this modification, the coil spring type wire 148 functions as the balancing counterweight 123.

While in the above-described constructions a pair of earpiece members 133A and 133B are used as the attachment members, it is also possible to additionally provide the subjective optometric apparatus 113 with a chin strap, which is hooked on the chin of the subject 114 as an auxiliary attachment member.

In the subjective optometric apparatus of this embodiment described above, it is possible for the subject to perform subjective optometry with a feel as if wearing a trial frame, without suffering the burden of the weight of the device.

[Others]

Incidentally, when performing optometry on the subject reading a magazine or the like with a subjective optometric apparatus according to the present invention being on his face, it is usual for the subject to slightly tilt his face downwards and to direct his eyes downwards. This tendency is conspicuous with a subject who has had an experience of wearing progressive lenses. However, in this case, the line of vision of the subject is deviated from the optical axis of the measurement lens, making it impossible to perform accurate measurement.

To cope with this, it is necessary to adopt an arrangement for matching the optical axis of the measurement lens with the line of vision. For example, in the case in which the subjective optometric apparatus is suspended as in the second embodiment, the above problem can be coped with by making the device capable of tilting with respect to the horizontal direction, arranging the optical unit of the device so as to be vertically movable, and moving the optical unit downwardly in accordance with the tilting angle when the device is tilted with respect to the horizontal direction. In the following, an example of a subjective optometric apparatus further equipped with such a construction will be described.

Figure 19:
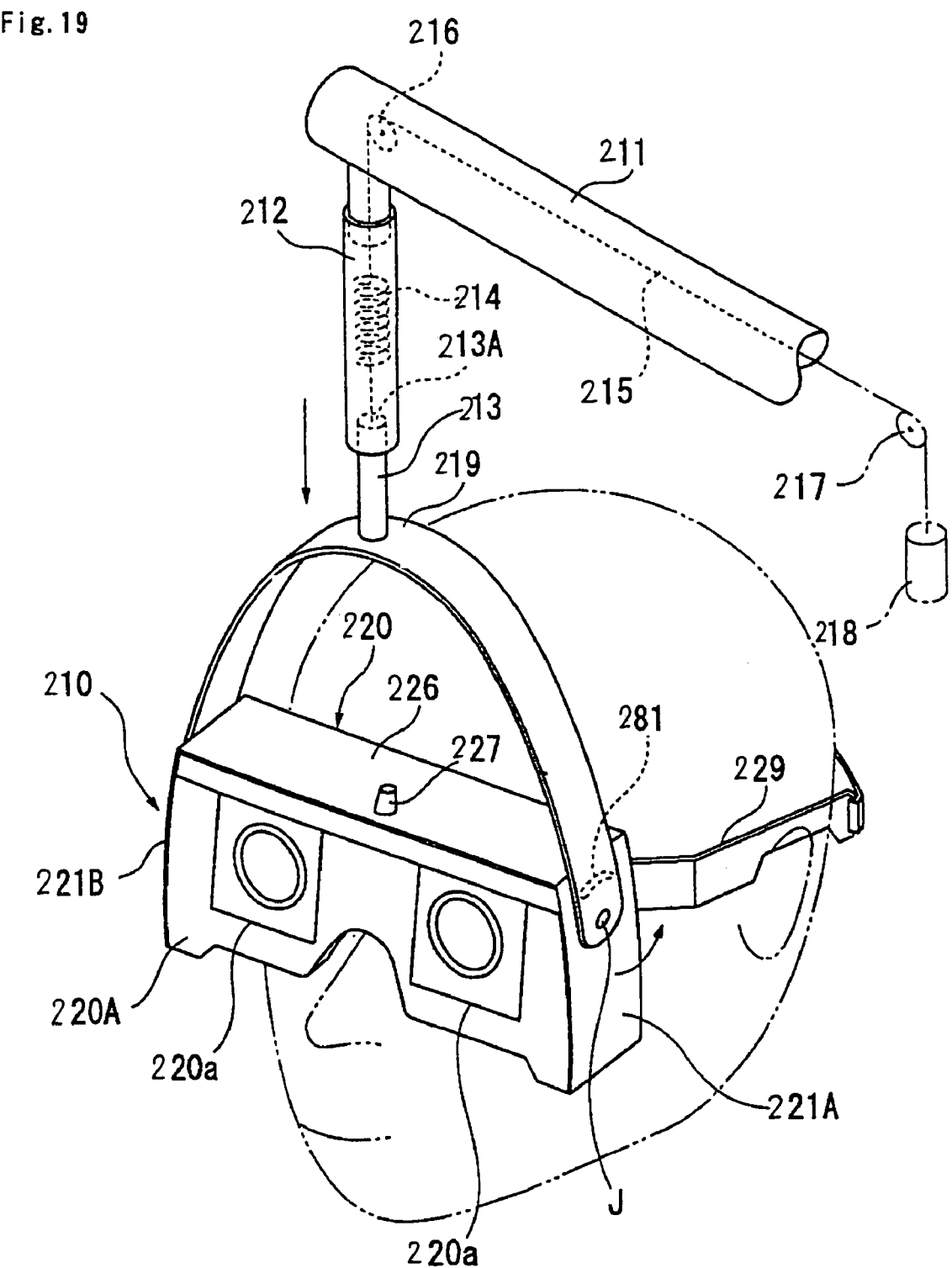
FIG. 19 is an explanatory view showing how the main body of a subjective optometric apparatus according to the present invention is suspended.

FIG. 19 shows a subjective optometric apparatus having a main body 210 suspended from an arm 211 mounted to an extendable post, as in the second embodiment described above. Mounted to the forward end portion of the arm 211 is a connection pipe 212 extending vertically downwards. An upper portion 213A of a connection shaft 213 is inserted into the connection pipe 212 so as to be vertically movable and rotatable. Further, the upper portion 213A of the connection shaft 213 is mounted to one end of a spring 214 arranged in the connection pipe 212, and the upper end of this spring 214 is connected to a wire 215. This wire 215 is wrapped around a pulley 216 provided in the arm 211 and is passed through the arm 211 to be further wrapped around a pulley 217 provided in the post. A balancing counterweight 218 is suspended from the pulley 217 side end of the wire 215.

Further, a reverse-U-shaped retaining member 219 is fixed to the lower portion of the connection shaft 213. The lower end portions of this retaining member 219 are pivoted to side wall portions 221A and 221B of a case 220 of the main body 210, enabling the main body 210 to rotate around the axis J with respect to the retaining member 219. The retaining member 219 is retained in the vertical state by the connection, pipe 212. Further, the main body 210 is suspended from the wire 215 through the intermediation of the retaining member 219, the connection shaft 213, and the spring 214, and the weight of the balancing counterweight 218 is equal to the total weight of the main body 210, the retaining member 219, the connection shaft 213, and the spring 214, whereby the weight of the main body 210, etc. is prevented from being applied to the subject wearing the main body 210.

Figure 20:
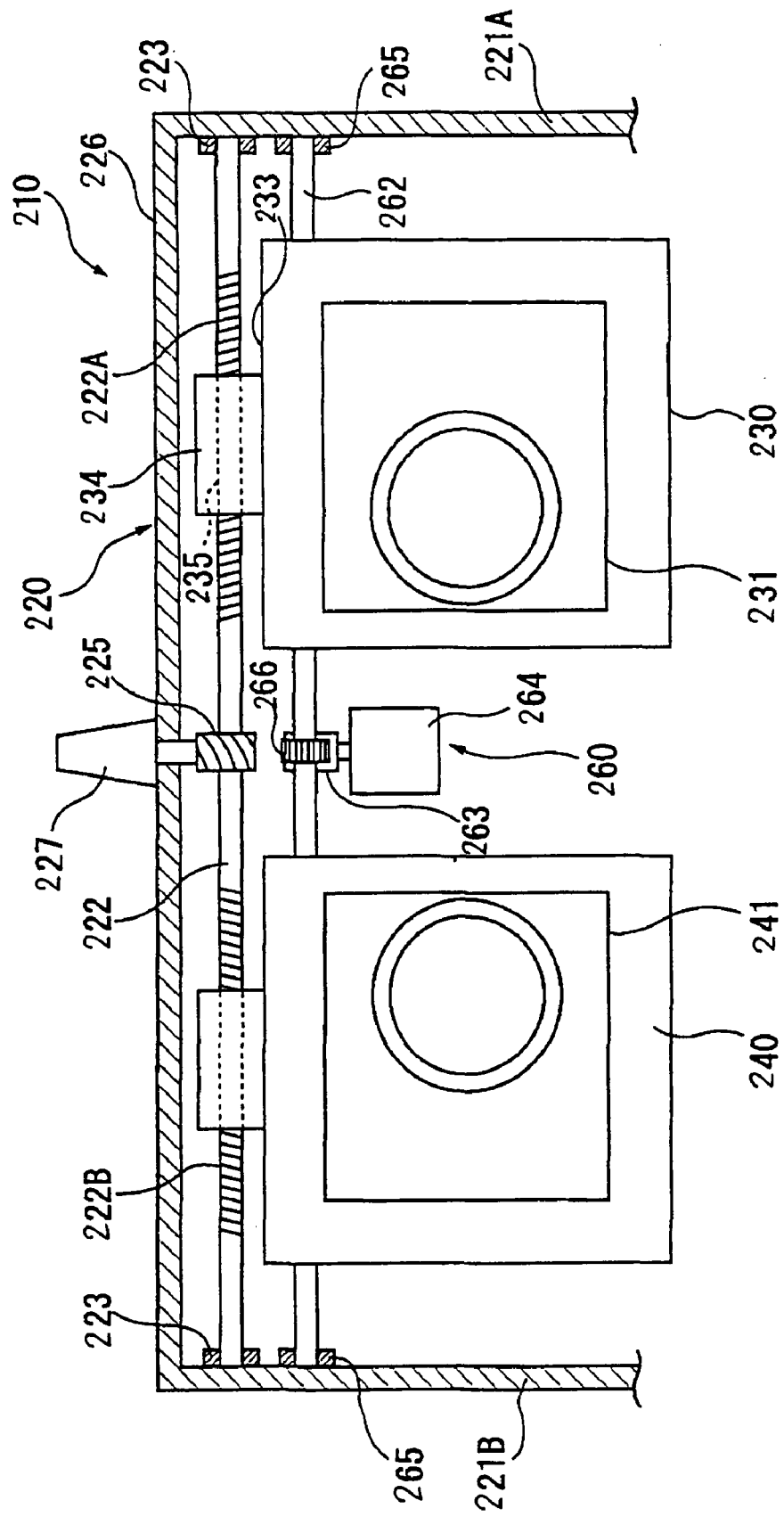
FIG. 20 is a front view of a retaining case of the subjective optometric apparatus shown in FIG. 19.
Figure 21:
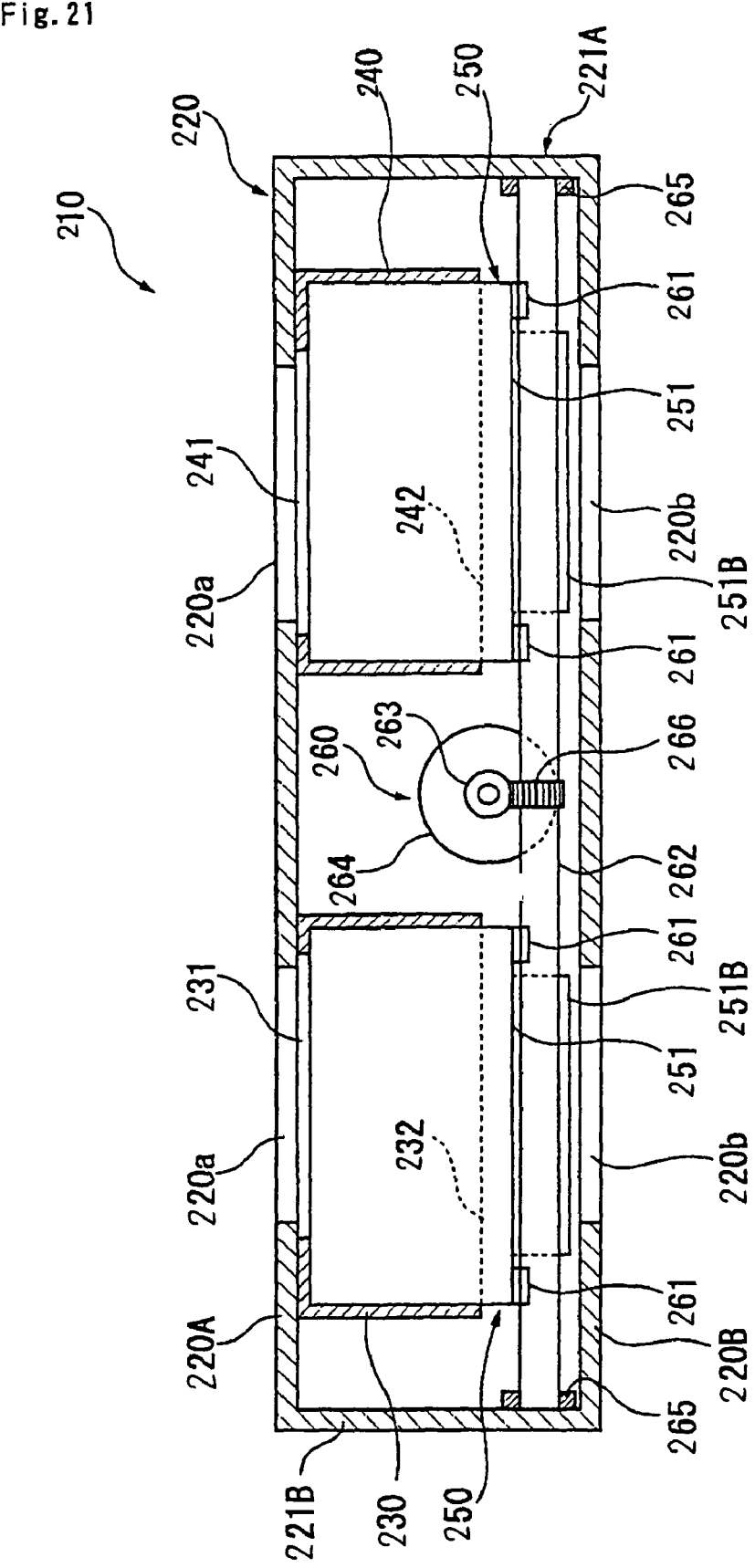
FIG. 21 is a plan sectional view showing the construction of the main body of a subjective optometric apparatus.
Figure 22:
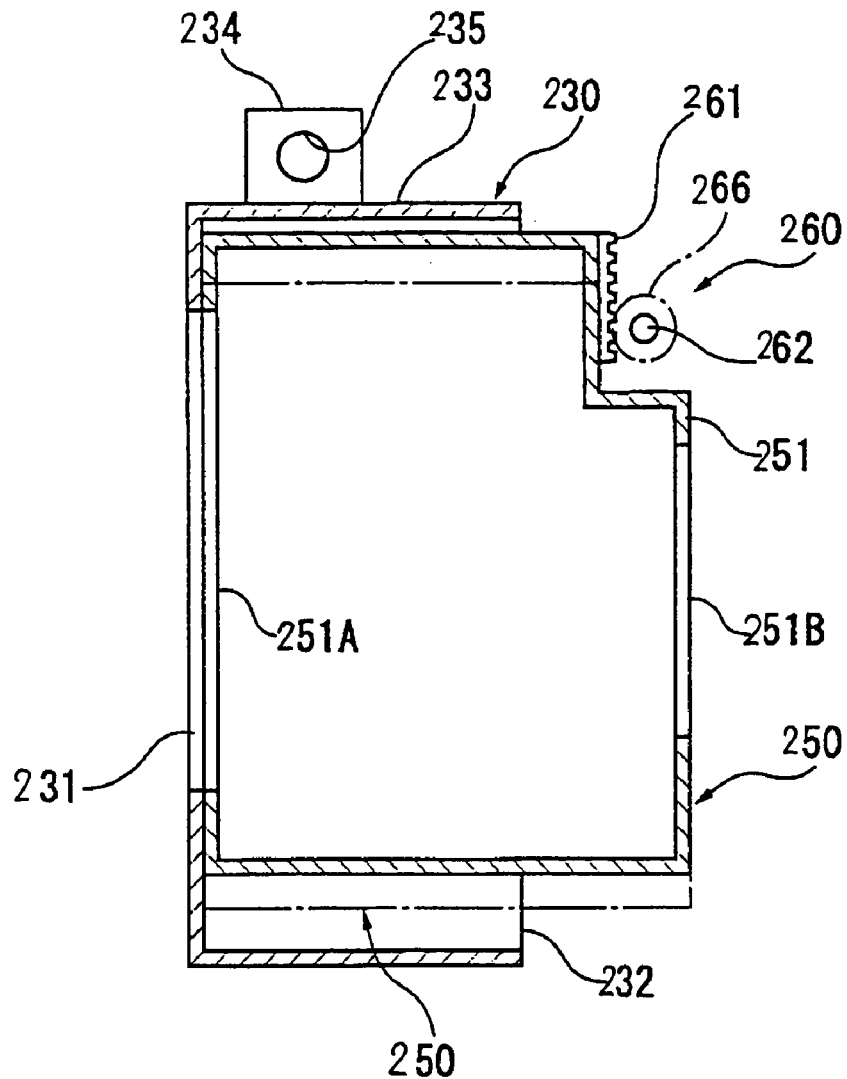
FIG. 22 is an explanatory view illustrating a structure for vertically moving an optical unit.

As shown in FIGS. 20 through 22, the main body 210 is equipped with the case 220, a pair of horizontally movable retaining cases 230 and 240 provided in the case 220, optical units 250 provided inside the retaining cases 230 and 240 so as to be vertically movable, a vertical movement mechanism 260 for vertically moving the optical units 250, a main body lock mechanism 270 for locking the main body 210, a tilt detecting means 280 for detecting tilting of the main body 210, etc.

Mounted to the case 220 is a head band 229 for attaching the main body 210 to the subject as shown in FIG. 19. Further, although not shown, the case 220 is equipped with a nose pad member and a forehead rest like those of the first embodiment. Further, a pair of openings 220a are formed in the front surface 220A of the case 220, and a pair of openings 220b are formed in the rear surface 220B of the case 220.

Figure 23:
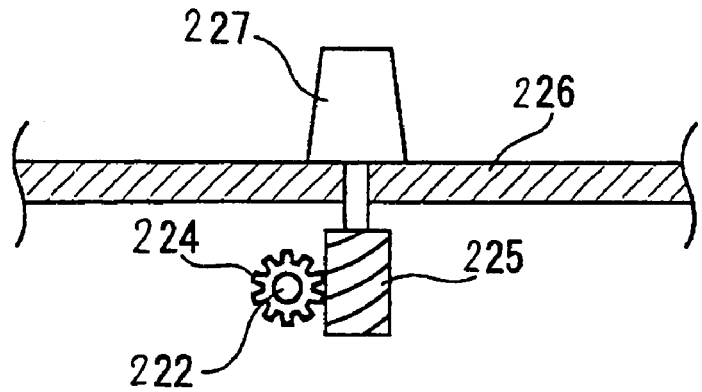
FIG. 23 is an explanatory view illustrating a structure for horizontally moving a retaining case.

Further, in the upper portion of the interior of the case 220, there is arranged a shaft 222 extending in the horizontal direction. The end portions of this shaft 222 are rotatably supported by bearing portions 223 provided on the side walls 221A and 221B of the case 220. The end portions of the shaft 222 are equipped with male screw portions 222A and 222B formed so as to be reverse to each other. Further, as shown in FIG. 23, a gear 224 is attached to the central portion of the shaft 222. This gear 224 is in mesh with a worm 225, which is adapted to rotate upon rotating operation on a knob 227 provided on the upper wall portion 226 of the case 220.

Figure 24:
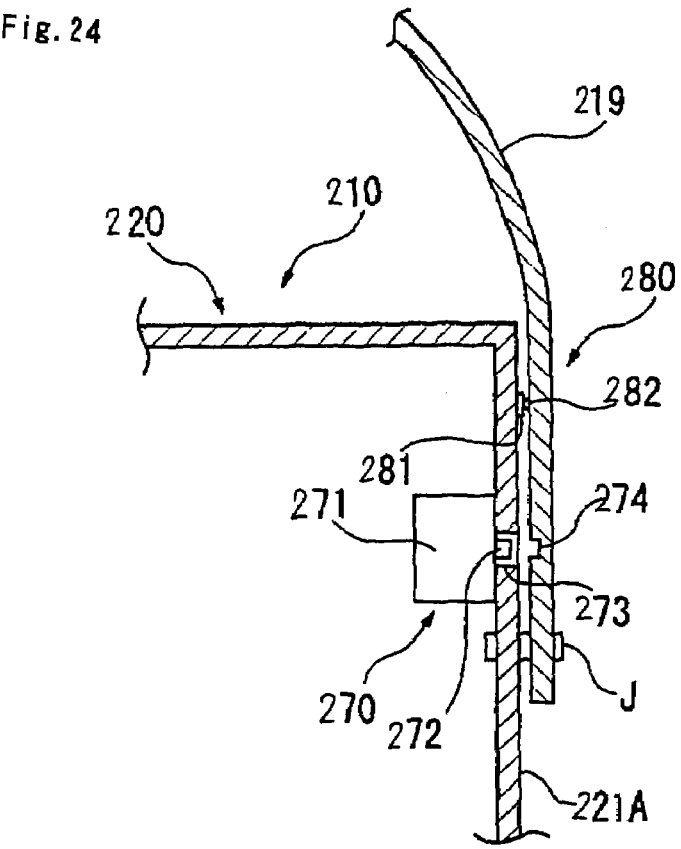
FIG. 24 is an explanatory view showing a structure in which the main body of a subjective optometric apparatus is rotatably mounted to a retaining member.
Figure 25:
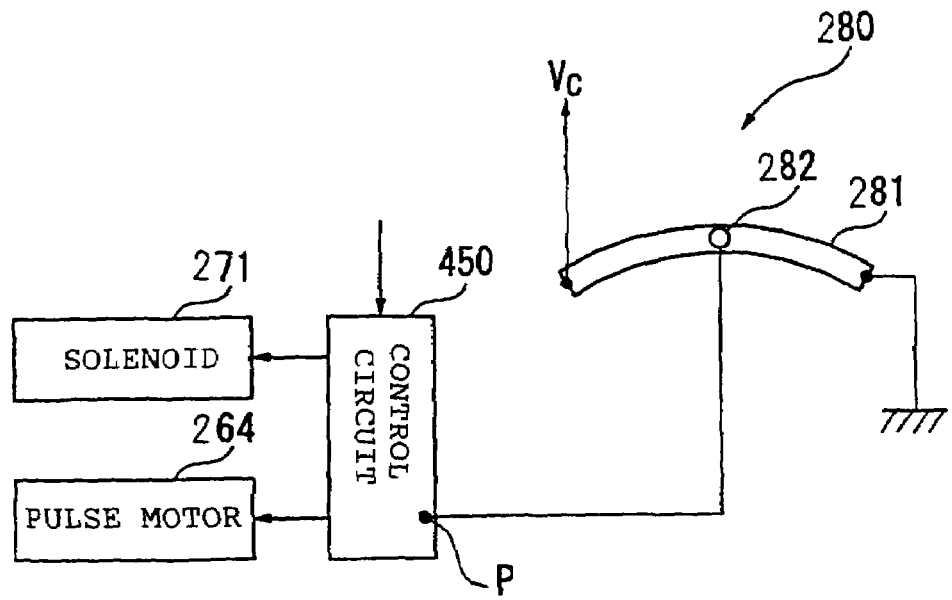
FIG. 25 is an explanatory view showing the construction of a tilt detecting means.

As shown in FIGS. 24 and 25, the tilt detecting means 280 is equipped with a slide resistor 281 provided on the side wall 221A of the case 220, and a contact 282 adapted to slide on the slide resistor 281. A voltage Vc is applied to one end of the slide resistor 281, whose other end is grounded. A contact 282 is provided on the inner side of the retaining member 219. Further, the contact 282 is connected to an input port P of a control circuit 450.

The contact 282 slides on the slide resistor 281 according to the tilting amount of the main body 210 with respect to the retaining member 219, and a voltage corresponding to its displacement position is input to the input port P of the control circuit 450. The control circuit 450 reads the input voltage, and obtains through computation the amount by which the main body 210 is tilted from the horizontal direction with respect to the retaining member 219.

Figure 26:
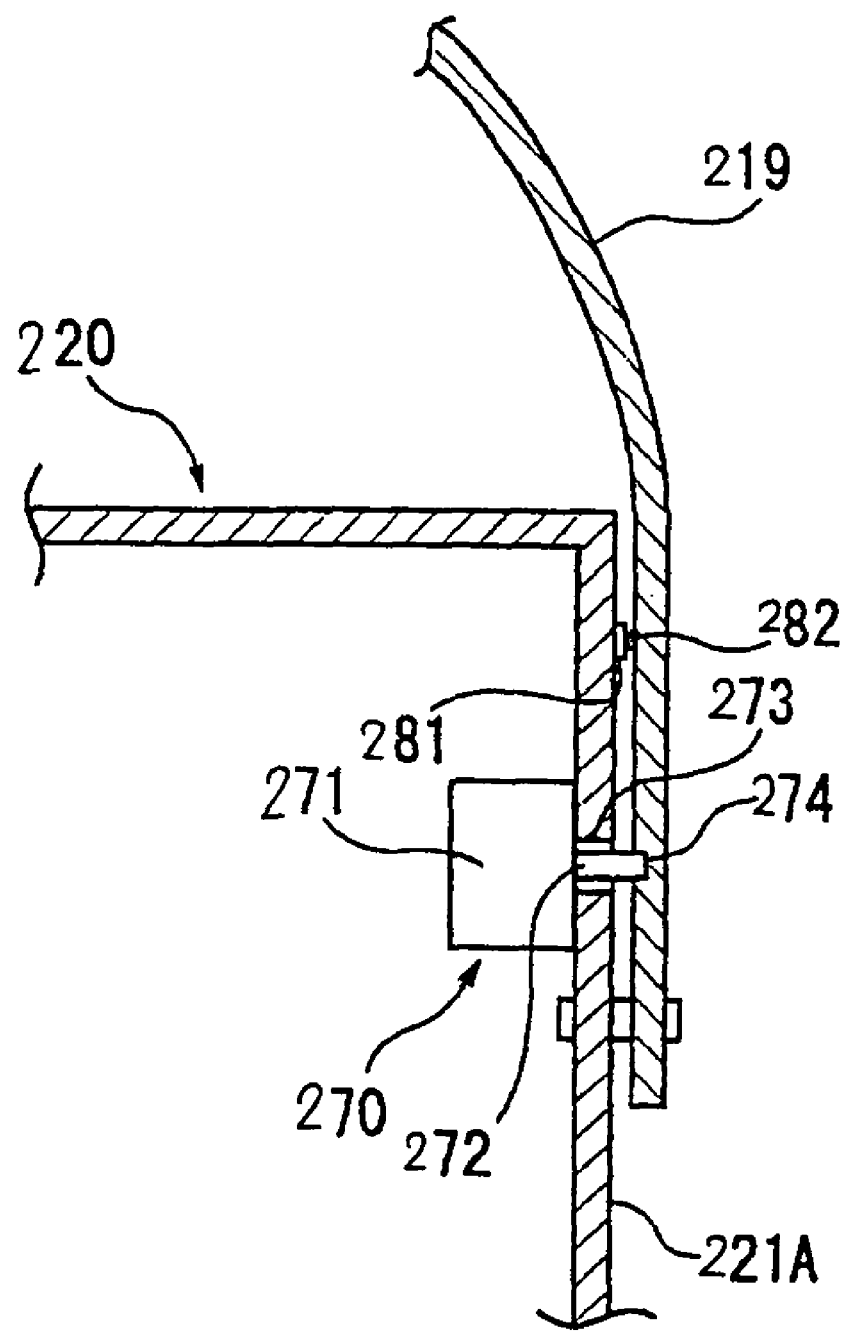
FIG. 26 is an explanatory view showing how the main body of a subjective optometric apparatus is locked.

As shown in FIG. 24, the main body lock mechanism 270 has a solenoid 271 provided in the case 220. As shown in FIG. 26, when this solenoid 271 operates, a rod 272 protrudes from a hole 273 of the case 220, and is engaged with a recess 274 provided on the inner side of the retaining member 219, whereby the main body 210 is locked in a state in which it does not tilt with respect to the retaining member 219.

As shown in FIGS. 20 through 22, the retaining case 230 is formed as a casing having openings 231 and 232 in the front and rear surfaces. The openings 231 and 232 are respectively opposed to the openings 220a and 220b of the case 220.

A rectangular protrusion 234 is formed on the top wall portion 233 of the retaining case 230. Formed in this protrusion 234 is a female screw 235 extending horizontally therethrough in FIG. 20. The shaft 222 is passed through this female screw 235, and the male screw 222A of the shaft 222 and the female screw 235 are threadedly engaged with each other. Upon rotating operation on the knob 227, the retaining case 230 is moved to the right or left according to the rotating direction of the shaft 222.

For example, when the shaft 222 is rotated clockwise as seen in FIG. 23, the retaining case 230 is moved to the right as seen in FIG. 20. Conversely, when the shaft 222 is rotated counterclockwise, the retaining case 230 is moved to the left.

The retaining case 240 has a construction similar to that of the retaining case 230. When the shaft 222 is rotated clockwise as seen in FIG. 23, the retaining case 240 is moved to the left as seen in FIG. 20, and when the shaft 222 is rotated counterclockwise as seen in FIG. 20, the retaining case 240 is moved to the right.

The distances through which the retaining cases 230 and 240 move upon rotating operation on the knob 227 are set to be the same.

As shown in FIG. 22, the optical unit 250 has a unit case 251 with openings 251A and 251B in the front and rear surfaces, a lens mounting frame 402 (See FIG. 27) provided in the unit case 251, an Alvarez lens 410 composed of a pair of optical elements 411 and 412, a Vcc lens 423, etc. The Alvarez lens 410 and the Vcc lens are mounted to the lens mounting frame 402 and constitute a measurement optical system. The opening 251A of the unit case 251 is opposed to the opening 231 of the retaining case 230, and the opening 251B is opposed to the opening 220b of the case 220. The unit case 251 of the retaining case 240 has a similar construction.

Figure 27:
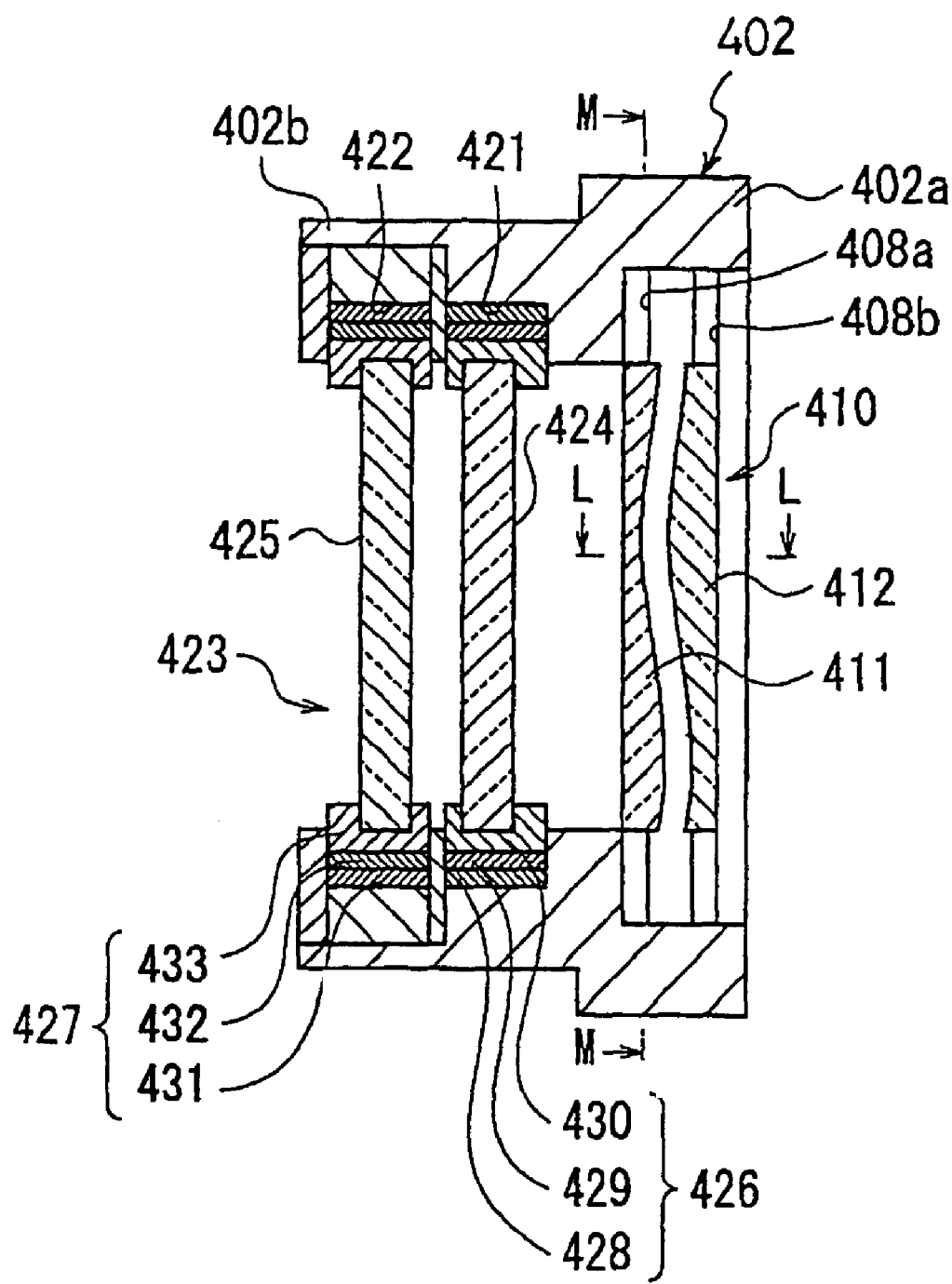
FIG. 27 is an explanatory view showing an arrangement of the lens system of an optical unit.

As shown in FIG. 27, the lens mounting frame 402 has a first lens mounting portion 402a and a second, cylindrical lens mounting portion 402b.

Figure 28:
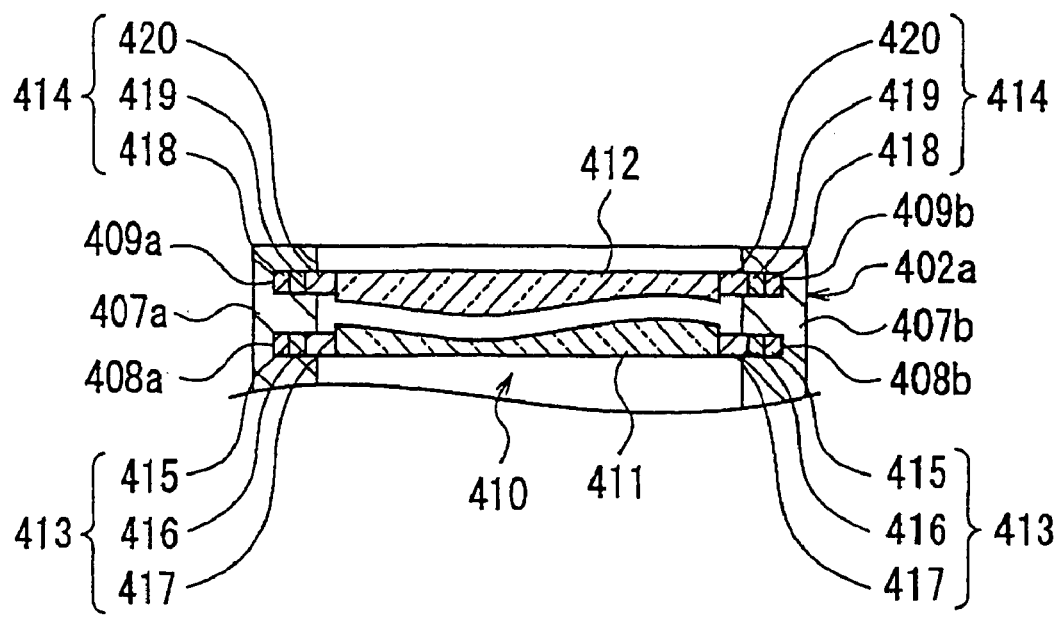
FIG. 28 is a cross-sectional view of the Alvarez lens portion taken along the line L—L of FIG. 27.
Figure 29:
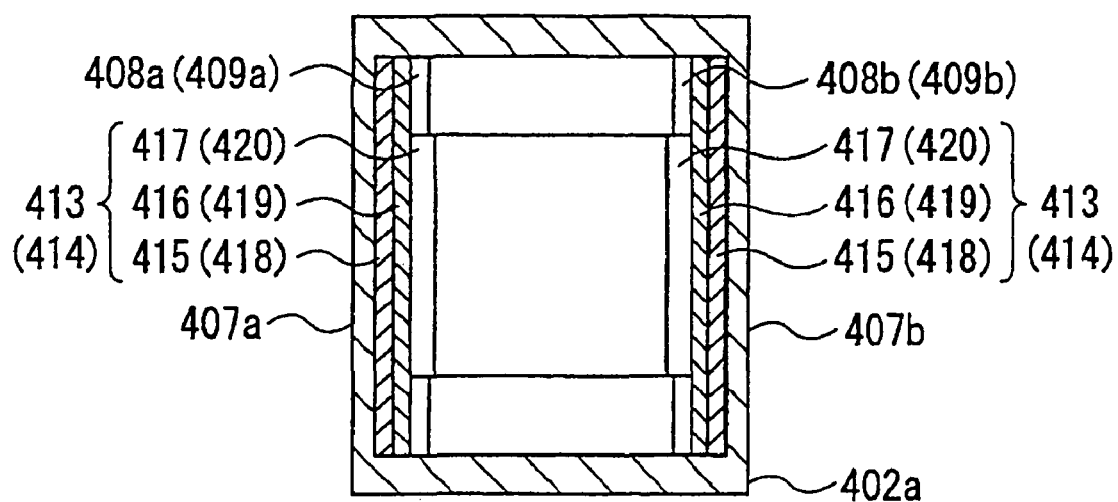
FIG. 29 is a longitudinal sectional view of the Alvarez lens portion taken along the line M—M of FIG. 27.

The first lens mounting portion 402a has left and right side wall portions 407a and 407b. The side wall portion 407a has vertically extending guide grooves 408a and 409a as shown in FIGS. 28 and 29. Similarly, the side wall portion 407b has vertically extending guide grooves 408b and 409b.

The Alvarez lens 410 is arranged between the side wall portions 407a and 407b. Further, ultrasonic linear motors (ultrasonic motors) 413 and 414 are respectively arranged in the guide grooves 408a and 408b.

The ultrasonic motor 413 has a piezoelectric element array 415 formed in a linear configuration by alternately connecting a multitude of electrodes and piezoelectric elements (not shown), a linear vibrating member (stator) 416 in which a multitude of teeth (not shown) are longitudinally arranged on the opposite side of the piezoelectric element array 415 and which is vibrated by the piezoelectric element array 415, and movable members 417 held in frictional contact with the multitude of teeth of the vibrator 416. The piezoelectric element array 415 is glued to the vibrating member 416. Further, the movable members 417 of the guide grooves 408a and 408b are fixed to the side portions of the optical element 411 of the Alvarez lens 410.

In this construction, the voltage applied to each electrode of the piezoelectric element array 415 is controlled to vary the phase of the bending standing-wave vibration (progressive wave) generated on the teeth side of the stator 416, whereby the movable members 417 are driven upwards or downwards by the teeth of the stator 416. In this way, the ultrasonic motor 413 may adopt a well-known construction.

Similarly, the ultrasonic motor 414 has a piezoelectric element array 418, a vibrating member (stator) 419, and movable members 420. The movable members 420 of the guide grooves 409a and 409b are fixed to the side portions of the optical element 412 of the Alvarez lens 410.

Figure 30:
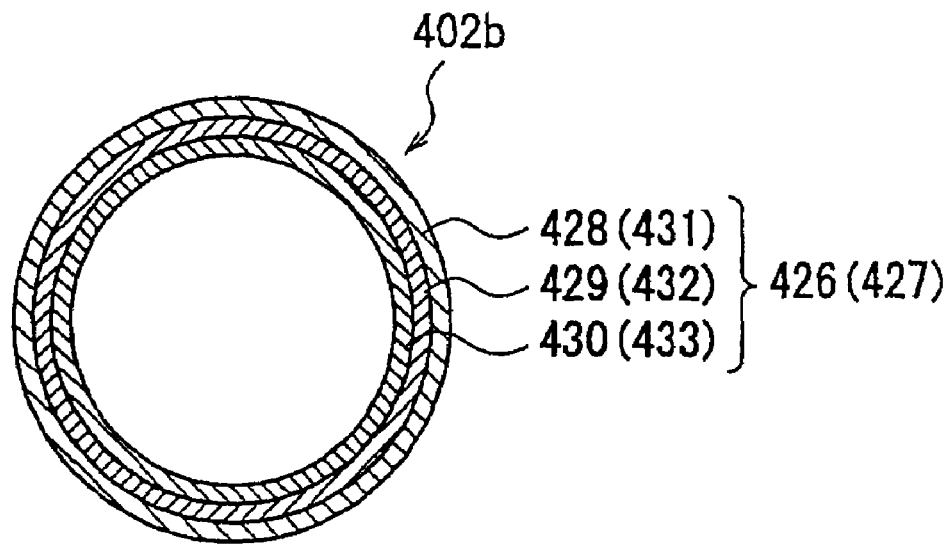
FIG. 30 is an explanatory view of the drive system of a Vcc lens.
Figure 31:
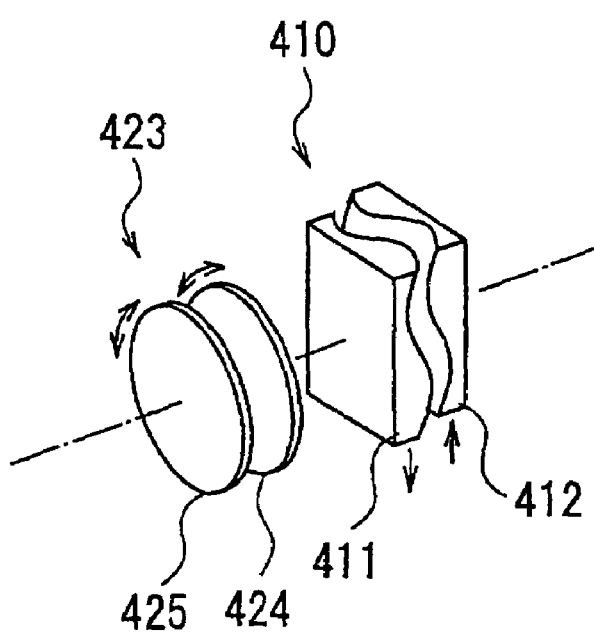
FIG. 31 is a perspective view illustrating the Alvarez lens and the Vcc lens of FIG. 27.

As shown in FIG. 30, the second lens mounting portion 402b is formed in a cylindrical configuration, and in the inner peripheral surface thereof, there are formed a pair of annular grooves 421 and 422 spaced apart from each other in the axial direction. Cylinder lenses 424 and 425 (See FIG. 31) of the Vcc lens 423 are rotated by ultrasonic motors 426 and 427 arranged in the annular grooves 421 and 422.

The ultrasonic motor 426 has a piezoelectric element array 428 formed in an annular configuration by alternately connecting a multitude of electrodes and piezoelectric elements (not shown), an annular vibrating member (stator) 429 having a multitude of teeth (not shown) arranged circumferentially on the opposite side of the piezoelectric element array 428 and adapted to be vibrated by the piezoelectric element array 428, and an annular movable member 417 held in frictional contact with the multitude of teeth of the vibrating member 429. The piezoelectric element array 428 is glued to the outer peripheral surface of the vibrating member 429. Further, a cylinder lens 424 is fixed in a movable member 430 of the annular groove 421.

In this construction, the voltage applied to each electrode of the piezoelectric element array 428 is controlled to vary the phase of the progressive wave generated on the teeth side of the stator 429, whereby the movable member 430 is caused to make normal or reverse rotation by the teeth of the stator 429. In this way, the ultrasonic motor 413 may adopt a well-known construction.

Similarly, the ultrasonic motor 427 has a piezoelectric element array 431, an annular vibrating member (stator) 432, and an annular movable member 433. The piezoelectric element array 431 is glued to the outer peripheral surface of the vibrating member 432. Further, a cylinder lens 425 is fixed in the movable member 433 of the annular groove 422.

As shown in FIGS. 20 through 22, the vertical movement mechanism 260 is composed of racks 261 provided on the right and left sides of the back surface of the unit case 251 of the optical unit 250, a spline shaft 262 extending horizontally (See FIG. 20) in the case 220, a worm 263, a pulse motor 264 for rotating the worm 263, etc.

The both end portions of the spline shaft 262 are rotatably retained by the bearing portions 265 provided in the side walls 221A and 221B of the case 220. Further, the spline shaft 262 has a groove (not shown) extending in the axial direction thereof. This groove is engaged with the rack 261, so that rotation of the spline shaft 262 causes the unit case 251 to move vertically with respect to the retaining cases 230 and 240. Further, the rack 261 is capable of making relative axial movement along the groove of the spline shaft 262, so that it does not hinder horizontal movement of the optical unit 250.

The worm 263 is in mesh with the gear 266 provided at the center of the spline shaft 262. The spline shaft 262 is rotated upon rotation of the worm 263 transmitted through the gear 266. Further, the pulse motor 264 is mounted in the case 220 through the intermediation of a bracket (not shown).

Figure 32:
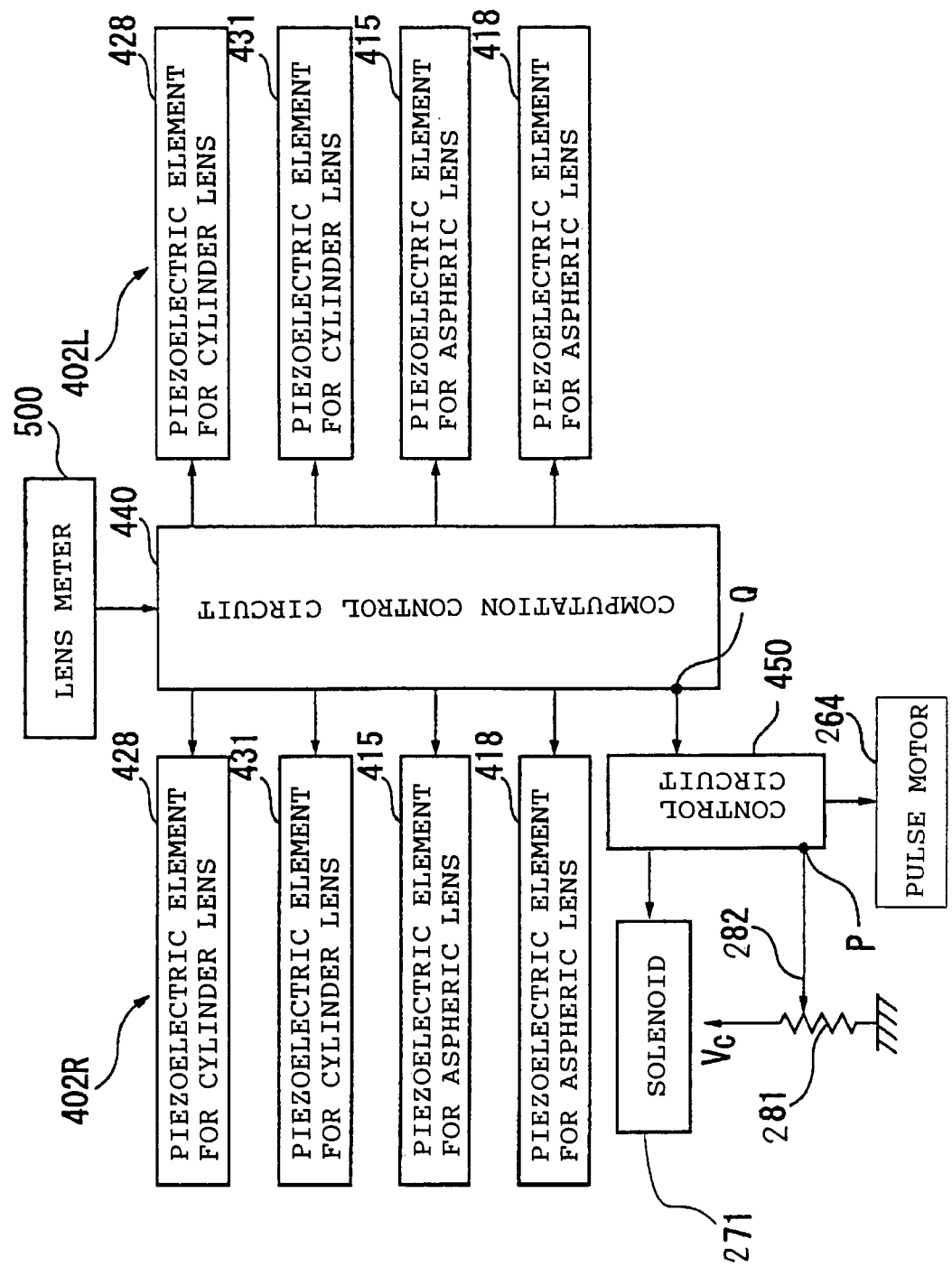
FIG. 32 is a block diagram showing the construction of the control system of a subjective optometric apparatus.

FIG. 32 shows the construction of the control system used in this subjective optometric apparatus.

Numeral 440 indicates a computation control circuit consisting of a CPU or the like. The computation control unit is mounted in an operation apparatus (not shown) having a keyboard or the like to be operated by the examiner. This computation control circuit 440 drive-controls the piezoelectric elements of the piezoelectric element arrays 415, 418, 428, and 431 in the lens mounting frames 402R and 402L mentioned above through a communication means (not shown). Here, the lens mounting frames 402R and 402L are respectively the lens mounting frames 402 of the optical units 250 for the right eye and the left eye. The above-mentioned communication means may be wireless or wired. Further, connected to the computation control circuit 440 are setting means, such as an operating means for setting or varying the spherical degree or for setting an axial angle of the cylindrical shaft, and a data input means. The setting means may consist of a keyboard, a mouse, or push-buttons (switches) for data setting. Further, it is also possible to use a means for taking in prescription data for glasses from other refractometers, lens meters or the like as the setting means.

Further, on the basis of measurement data obtained by a lens meter 500, the computation control circuit 440 makes a judgment as to whether the lens to be examined (not shown) is a progressive lens or a single lens. When it is determined that the lens to be examined is progressive, a signal indicating that it is a progressive lens (a progressive signal) is output from an output port Q.

On the basis of the voltage at the input port P and the progressive signal from the computation control circuit 440, a control circuit 450 controls the pulse motor 264 to vertically move the optical unit 250, and controls the solenoid 271 to lock the main body 210. While this control circuit 450 is provided inside the case 220 as described above, it may also be mounted in the operation apparatus like the computation control circuit 440.

Next, the operation of the subjective optometric apparatus, constructed as described above, will be described.

First, as shown in FIG. 1, the main body 210 is attached to the subject by using the head band 229. Then, the examiner operates the knob 227 to move the retaining cases 230 and 240 horizontally to match the optical axis of the optical unit 250 to the position of each pupil of the subject.

Next, as in the prior art, a target is presented by a target presenting device (not shown), and the examiner asks the subject about the way the target presented by the target presenting device looks as he causes relative vertical movement of the optical elements 411 and 412 of the Alvarez lens 410 and rotates the cylinder lenses 424 and 425 of the Vcc lens 423, thereby measuring the optical characteristics of the eye to be examined (i.e., performing far vision test) to obtain the prescription values.

When the far vision test on the eye to be examined has been completed, checking is made on how a nearby object can be seen through the lens as prescribed while the subject is reading a magazine or the like (near vision test).

When reading a magazine or the like, the subject directs his face slightly downwards. At this time, with a subject with no experience of wearing progressive lenses, the inclination of the face is generally somewhat larger as compared with that of a subject with such experience (of wearing progressive lenses).

The main body 210 rotates around the axis J of the retaining member 219 in correspondence with the inclination of the face of the subject, and is inclined with respect to the horizontal direction. Due to this inclination, the contact 282 of the retaining member 219 slides on the slide resistor 281, and a voltage corresponding to the moving position of the contact 282 is input to the input port P of the control circuit 450. That is, the tilt detecting means 280 outputs a voltage (detection signal) corresponding to the inclination angle of the main body 210 to be detected, and the control circuit 450 reads this detection signal input to the input port P to thereby obtain the inclination angle (tilting amount) of the main body 210.

When the inclination angle α obtained is relatively large, that is, when it is larger than the (second) threshold value E2, the control circuit 450 judges that the subject has no experience of wearing progressive lenses, and maintains the pulse motor 264 in the non-operating state. In this case, the optical unit 250 keeps the position as shown in FIG. 22.

When the inclination angle β obtained is small, that is, when the inclination angle β is larger than a (first) threshold value E1 (<E2) and smaller than the threshold value E2 (E1<β<E2), the control circuit 450 judges that the subjective has an experience of wearing progressive lenses, and operates the pulse motor 264, moving the optical unit 250 downwardly from the position shown in FIG. 22 by a distance corresponding to the inclination angle β. That is, the optical unit 250 is moved to the chain-line position shown in FIG. 22. By this downward movement of the optical unit 250, the subject with an experience of wearing progressive lenses can look at a magazine or the like through the optical axis portion of the measurement optical system of the optical unit 250, so that it is possible to perform measurement in a natural state. Thus, it is possible to accurately determine the power of the near vision part of the progressive lens.

When the inclination angle detected by the tilt detecting means 280 is larger than the threshold value E1, the optical unit 250 may be moved downwardly by a fixed distance.

When the measurement data on the lens obtained by the lens meter 500 is input, the computation control circuit 440 makes a judgment, from this data, as to whether the lens concerned is a progressive lens or a single lens, making a judgment as to whether the subject has an experience of wearing progressive lenses or not. When it is determined that the subject has such experience, the computation control circuit 440 outputs a progressive signal from the output port Q.

Upon receiving the progressive signal from the computation control circuit 440, the control circuit 450 operates the solenoid 271, and causes the rod 272 to be engaged with the recess 274 of the retaining member 219, whereby the main body 210 is locked so as not to tilt with respect to the retaining member 219. As a result, the face of the subject is maintained in the horizontal state, so that the subject can fix his eye on the target presented in the horizontal direction, with the line of vision being stable and without feeling the weight of the main body 210.

In particular, when performing optometry on an infant or an aged person, it is difficult to maintain the face in a fixed state. With the above construction, however, it is possible to maintain the face in a fixed state without involving any pain.

When near vision test is to be performed after performing far vision test in this state, this locked state is canceled.

As has been described in detail, in the subjective optometric apparatus according to the first aspect of the present invention, by placing the earpiece members on the ears of the subject and by holding the nose pad member in contact with the nose of the subject, it is possible for the subject to wear the main body of the subjective optometric apparatus on the face like a trial frame, whereby both far vision test and near vision test can be performed.

Further, solely by a single operation of switching the earpiece members and the nose pad member between the locked and unlocked state by the lock mechanism, it is possible to fit the subjective optometric apparatus to the subject.

Thus, it is possible to perform adjustment for each subject by a simple operation and in a very short time, whereby the burden on the operator is relieved, and the subject is spared excessive stress.

Further, in the subjective optometric apparatus according to the second aspect of the present invention, it is possible to abut, in addition to the earpiece members and nose padmember, the forehead rest member to the face (forehead) of the subject, whereby, the subjective optometric apparatus is in more intimate contact with the face, thereby preventing the subjective optometric apparatus from slipping down.

Further, the switching between the locked and unlocked state of the forehead rest member by the lock mechanism is operationally connected with the switching between the locked and unlocked state of the earpiece members and the nose pad member, whereby an increase in the operational burden on the operator is avoided.

Further, in the subjective optometric apparatus according to the third aspect of the present invention, due to the provision of the earpiece members and the forehead rest member, it is possible for the subject to wear the main body of the subjective optometric apparatus on the face like a trial frame, whereby both far vision test and near vision test can be performed Further, solely by a single operation of switching the earpiece members and the forehead rest member between the locked and unlocked state by the lock mechanism, it is possible to fit the subjective optometric apparatus to the subject.

Thus, it is possible to perform adjustment for each subject by a simple operation and in a very short time, whereby the burden on the operator is relieved, and the subject is spared excessive stress.

Further, in the subjective optometric apparatus according to the fourth aspect of the present invention, the operator attaches the subjective optometric apparatus to the subject, with the lock mechanism being retained in the unlocked state against the biasing force of the biasing means, and the lock mechanism is automatically restored to the locked state by the biasing means by canceling this retention. As a result, it is possible to achieve an improvement in operability for the lock mechanism.

What is claimed is:

1. A subjective optometric apparatus comprising:
   a main body;
   an Alvarez lens provided in the main body, the Alvarez lens having its refraction characteristics continuously changed in response to relative displacement of a pair of optical elements;
   earpiece members to be placed on the ears of a subject and a nose pad member to be held in contact with the nose of the subject, the earpiece members and the nose pad member being provided on the main body and having fixed movable ranges so as to allow adjustment according to a positional relationship between the ears and the nose of the subject; and
   a lock mechanism for switching the earpiece members and the nose pad member with a single operation between an unlocked state which allows the earpiece members and the nose pad member to move freely within the movable ranges and a locked state in which the earpiece members and the nose pad member are fixed at desired positions within the movable ranges.

2. A subjective optometric apparatus according to claim 1, wherein the main body is equipped with a forehead rest member to be held in contact with the forehead of the subject when the main body is attached to the subject, wherein the forehead rest member has a fixed movable range which allows its adjustment according to a positional relationship between the forehead rest member and the forehead of the subject, and wherein the lock mechanism switches, in synchronization with the switching of the earpiece members and the nose pad member between the unlocked state and the locked state, the forehead rest member between an unlocked state which allows the forehead rest member to move freely within the movable range and a locked state in which the forehead rest member is fixed at a desired position within the movable range.

3. A subjective optometric apparatus comprising:
a main body;
an Alvarez lens provided in the main body, the Alvarez lens having its refraction characteristics continuously changed in response to relative displacement of a pair of optical elements;

earpiece members to be placed on the ears of a subject and a forehead rest member to be held in contact with the forehead of the subject, the earpiece members and the forehead rest member being provided on the main body and having fixed movable ranges so as to allow adjustment according to a positional relationship between the ears and the forehead of the subject; and a lock mechanism for switching the earpiece members and the forehead rest member with a single operation between an unlocked state which allows the earpiece members and the forehead rest member to move freely within the movable ranges and a locked state in which the earpiece members and the forehead rest member are fixed at desired positions within the movable ranges.

4. A subjective optometric apparatus according to any one of claims 1 to 3, wherein the lock mechanism comprises biasing means for biasing the device to be in the locked state.

* * * * *